US007879365B2

(12) United States Patent
Modak et al.

(10) Patent No.: US 7,879,365 B2
(45) Date of Patent: Feb. 1, 2011

(54) ZINC SALT COMPOSITIONS FOR THE PREVENTION OF DERMAL AND MUCOSAL IRRITATION

(75) Inventors: Shanta M. Modak, River Edge, NJ (US); Trupti Gaonkar, New York, NY (US); Milind Shintre, New York, NY (US); Lauserpina Caraos, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 877 days.

(21) Appl. No.: 10/892,034

(22) Filed: Jul. 15, 2004

(65) Prior Publication Data

US 2005/0048139 A1    Mar. 3, 2005

Related U.S. Application Data

(63) Continuation-in-part of application No. 10/622,272, filed on Jul. 17, 2003, which is a continuation-in-part of application No. PCT/US03/03896, filed on Feb. 7, 2003.

(60) Provisional application No. 60/355,549, filed on Feb. 7, 2002.

(51) Int. Cl.
   *A01N 59/16*    (2006.01)
   *A61K 31/60*    (2006.01)

(52) U.S. Cl. .................. 424/642; 424/641; 514/159

(58) Field of Classification Search .............. 514/159; 424/641, 642
   See application file for complete search history.

(56) References Cited

U.S. PATENT DOCUMENTS

| 3,485,915 | A | | 12/1969 | Gerstein et al. ............. 424/81 |
|---|---|---|---|---|
| 4,318,907 | A | * | 3/1982 | Kligman et al. ............ 514/164 |
| 4,478,853 | A | | 10/1984 | Chaussee .................... 424/358 |
| 4,853,978 | A | | 8/1989 | Stockum ........................ 2/167 |
| 4,889,844 | A | | 12/1989 | Silvetti, Sr. et al. ........... 514/60 |
| 4,910,205 | A | * | 3/1990 | Kogan et al. ................ 514/290 |
| 4,956,170 | A | | 9/1990 | Lee ............................. 424/81 |
| 4,963,591 | A | | 10/1990 | Fourman et al. |
| 4,966,754 | A | * | 10/1990 | Purohit et al. ............... 424/401 |
| 5,059,416 | A | | 10/1991 | Cherukuri et al. ............. 424/48 |
| 5,116,602 | A | | 5/1992 | Robinson et al. |
| 5,133,090 | A | | 7/1992 | Modak et al. .................. 2/168 |
| 5,208,031 | A | | 5/1993 | Kelly .......................... 424/412 |
| 5,357,636 | A | | 10/1994 | Dresdner, Jr. et al. ........ 2/161.7 |
| 5,403,864 | A | | 4/1995 | Bruch et al. ................. 514/721 |
| 5,447,930 | A | | 9/1995 | Nayak |
| 5,516,510 | A | | 5/1996 | Beilfuss et al. ............... 424/65 |
| 5,591,442 | A | | 1/1997 | Diehl et al. .................. 424/401 |
| 5,624,675 | A | | 4/1997 | Kelly |
| 5,648,389 | A | * | 7/1997 | Gans et al. ................... 514/557 |
| 5,658,575 | A | * | 8/1997 | Ribier et al. ................. 424/401 |
| 5,705,532 | A | | 1/1998 | Modak et al. ................ 514/635 |
| 5,708,023 | A | | 1/1998 | Modak et al. ................ 514/494 |
| 5,753,270 | A | | 5/1998 | Beauchamp et al. |
| 5,776,430 | A | | 7/1998 | Osborne et al. ............... 424/43 |
| 5,885,562 | A | | 3/1999 | Lowry et al. .................. 424/65 |
| 5,951,993 | A | | 9/1999 | Scholz et al. ................ 424/405 |
| 5,965,137 | A | * | 10/1999 | Petrus ......................... 424/756 |
| 5,965,610 | A | | 10/1999 | Modak et al. ................ 514/494 |
| 5,980,477 | A | | 11/1999 | Kelly ........................... 602/77 |
| 5,985,918 | A | | 11/1999 | Modak et al. ................ 514/494 |
| 6,022,551 | A | | 2/2000 | Jampani et al. .............. 424/405 |
| 6,037,386 | A | | 3/2000 | Modak et al. ................ 524/105 |
| 6,040,347 | A | * | 3/2000 | Cupferman et al. ......... 514/723 |
| 6,107,261 | A | | 8/2000 | Taylor et al. ................. 510/131 |
| 6,136,771 | A | | 10/2000 | Taylor et al. ................. 510/388 |
| 6,187,327 | B1 | | 2/2001 | Stack .......................... 424/405 |
| 6,204,230 | B1 | | 3/2001 | Taylor et al. ................. 510/131 |
| 6,287,577 | B1 | * | 9/2001 | Beerse et al. ................ 424/401 |
| 6,321,750 | B1 | | 11/2001 | Kelly |
| 6,344,218 | B1 | | 2/2002 | Dodd |
| 6,352,701 | B1 | | 3/2002 | Scholz et al. ................ 424/405 |
| 6,387,357 | B1 | | 5/2002 | Chopra et al. ................. 424/65 |
| 6,403,067 | B1 | * | 6/2002 | Schamper et al. ............. 424/65 |
| 6,426,062 | B1 | | 7/2002 | Chopra et al. ................. 424/65 |
| 6,485,716 | B1 | | 11/2002 | Fei et al. |
| 6,723,689 | B1 | | 4/2004 | Hoang et al. |
| 6,846,846 | B2 | * | 1/2005 | Modak et al. ................ 514/722 |
| 2003/0134780 | A1 | * | 7/2003 | Patt ............................. 514/6 |
| 2003/0152644 | A1 | | 8/2003 | Modak et al. |
| 2005/0019431 | A1 | | 1/2005 | Modak et al. |
| 2006/0141017 | A1 | | 6/2006 | Kling et al. |

FOREIGN PATENT DOCUMENTS

| DE | 4140474 | 6/1993 |
|---|---|---|
| DE | 4240674 | 3/1994 |
| DE | 19523320 | 1/1997 |
| EP | 0041448 | 12/1981 |
| EP | 304802 | 3/1989 |

(Continued)

OTHER PUBLICATIONS

Ebner et al. Am. J. Clin. Dermatol., 2002, vol. 3, No. 6, pp. 427-433.*
Cimiotti JP, Marmur ES, Nesin M, Hamlin-Cook P, Larson EL. Adverse reactions associated with an alcohol-based hand antiseptic among nurses in a neonatal intensive care unit. *Am. J. Infect. Control* 2003:131:43-48.

(Continued)

*Primary Examiner*—James D Anderson
(74) *Attorney, Agent, or Firm*—Baker Botts LLP

(57) ABSTRACT

The present invention provides for compositions and methods that may offer protection from irritants as well as antimicrobial protection. Preferred embodiments of the invention include topical antimicrobial compositions that lack conventional antibiotics or preservatives, wherein the antimicrobial benefit is created by essential oils (or their active ingredients), emollient solvents and, in some instances, anti-inflammatory agents.

4 Claims, No Drawings

FOREIGN PATENT DOCUMENTS

| | | |
|---|---|---|
| EP | 402078 | 9/1992 |
| EP | 0521455 | 1/1993 |
| EP | 0604848 | 7/1994 |
| EP | 06045848 | 7/1994 |
| EP | 0674896 | 10/1995 |
| EP | 0694310 | 1/1996 |
| EP | 0313302 | 4/1998 |
| EP | 1001012 | 5/2000 |
| FR | 2729050 | 7/1996 |
| JP | 10328284 | 12/1998 |
| RU | 2166309 | 5/2001 |
| SU | 833240 | 5/1981 |
| WO | WO8400111 | 1/1984 |
| WO | WO8704350 | 7/1987 |
| WO | WO8800795 | 2/1988 |
| WO | WO8803799 | 6/1988 |
| WO | WO8905645 | 6/1989 |
| WO | WO9307903 | 4/1993 |
| WO | WO9318745 | 9/1993 |
| WO | WO9318852 | 9/1993 |
| WO | WO9415461 | 7/1994 |
| WO | WO 94/18939 | 9/1994 |
| WO | WO9526134 | 10/1995 |
| WO | WO9824426 | 6/1998 |
| WO | WO9851275 | 11/1998 |
| WO | WO9903463 | 1/1999 |
| WO | WO99/38505 | 5/1999 |
| WO | WO9938505 | 8/1999 |
| WO | WO 99/51192 | 10/1999 |
| WO | WO9960852 | 12/1999 |
| WO | WO9963816 | 12/1999 |
| WO | WO0037042 | 6/2000 |
| WO | WO0141573 | 6/2001 |
| WO | WO03003896 | 1/2003 |
| WO | 03034994 | 5/2003 |
| WO | WO03034994 | 5/2003 |
| WO | 03003896 | 8/2003 |
| WO | WO 03/066001 A2 | 8/2003 |
| WO | WO03066001 | 8/2003 |
| WO | WO03083028 | 10/2003 |
| WO | WO2004014416 | 2/2004 |
| WO | WO2006099359 | 9/2006 |
| WO | WO2007069214 | 6/2007 |

OTHER PUBLICATIONS

Bleasel N, Tate B, Rademaker M. Allergic contact dermatitis following exposure to essential oils. *Australian Journal of Dermatology* 2002;43:211-213.

Vilaplana J, Romaguera C. Contact dermatitis from the essential oil of tangerine in fragrances. *Contact Dermatitis* 2002;46:108.

Nair B. Final report on the safety assessment of Mentha Piperita (Peppermint) oil, Mentha Piperita (Peppermint) Leaf extract, Mentha Piperita (Peppermint) leaf and Mentha Piperita (Peppermint) water. *International Journal of Toxicology* 2001;20(Suppl 3):61-73.

Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). *Contact Dermatitis* 2001;44:344-346.

Wohrl S, Hemmer W, Focke M, Gotz M, Jarisch R. The significance of fragrance mix, balsam of Peru, colophony and propolis as screening tools in the detection of fragrance allergy. *British Journal of Dermatology* 2001;145(2):268-273.

Sugiura M, Hayakawa R, Kato Y, Sugiura K, Hashimoto R. Results of patch testing with lavender oils in Japan. *Contact Dermatitis* 2000;43:157-160.

De Groot A, Frosch PJ. Adverse reactions to fragrances: a clinical review. *Contact Dermatitis* 1997;36:57-86.

Modak et al., 2005, A topical cream containing a zinc gel (allergy guard) as a prophylactic against latex glove-related contact dermatitis. Dermatitis. 16(1):22-7.

Modak SM, et al., A Topical Zinc Gluconate Gel Composition for the Prevention of latex/Starch Glove Related Allergic Reactions: Pilot Study in Volunteers. In: Programs and Abstracts of the 37th Interscience Conference on Antimicrobial Agents and Chemotherapy, Toronto: 1997; American Society for Microbiology Washington DC, Abstract J-52.

Goodman and Gilman's The Pharmacological Basis of Therapeutics (Goodman Gilman A, Rall TW, Nies AS, Taylor P, ed. (Pergamon Press; Elmsford, N.Y.: 1990).

Bush et al., 1986, "Pig skin as test substrate for evaluating topical antimicrobial activity" J Clin Microbiol 24:343-348.

Meyer et al., 1978, "The skin of domestic mammals as a model for the human skin, with special reference to the domestic pig." Curr. Problem Dematol 7:39-52.

Lansdown, "Interspecies variations in response to topical application of selected zinc compounds," Food Chem Toxicol. Jan. 1991;29(1):57-64.

Rosenthal, S.L.; Effect of Medicaments on the Motility of the Oral Flora with Special Reference to the Treatment of Vincent's Infection; II. Journal of Dental Research; 1943; vol. 22, pp. 491-494.

3M Avagard Surgical and Healthcare Personnel Hand Antiseptic with Moisturizers news release, 3M Company, Jun. 11, 2001.

3M Avagard Surgical and Healthcare Personnel Hand Antiseptic with Moisturizers product description, 3M Company, 2001.

A-Z of exhibitors; at Central European Coatings Show, PPC1. Polymers Paint Colour Journal, No. 4433, vol. 190, p. 42, Oct. 1, 2000.

Beilfuss, "A multifunctional ingredient for deodorants," SOFW Journal, 1998, vol. 124, p. 360, 362-364, 366.

Bezic et al., 2003, Composition and antimicrobial activity of *Achillea clavennae* L. essential oil. Phytother. Res. 17(9):1037-1040.

Bleasel et al., 2002, "Allergic contact dermatitis following exposure to essential oils" Australian Journal of Dermatology 43:211-213.

Brehm-Stecher et al. 2003, Sensitization of *Staphylococcus aureus* and *Escherichia coli* to antibiotics by the sesquiterpenoids nerolidol, farnesol, bisabolol, and apritone. Antimicrobial Agents and Chemotherapy, 47(10):3357-3360.

Cimiotti et al., 2003, "Adverse reactions associated with an alcohol-based hand antiseptic among nurses in a neonatal intensive care unit." Am. J. Infect. Control 31 :43-48.

de Abreu Gonzaga et al., "Composition and antibacterial activity of the essential oils from *Zanthoxylum rhoifolium*." 2003, Planta Med. 69(8):773-775.

De Groot A, Frosch PJ. Adverse reactions to fragrances: a clinical review. Contact Dermatitis 1997;36:57-86.

"Drug Information for the Health Care Professional," vol. 1A, USP-D1, 1989, Ninth Edition, pp. 792-793, Banta Company, VIR. s.

Fitzgerald, K.A., Davies, A., and Russel, A.D., "Mechanism of Action of Chlorhexidine Diacitate and Phenoxyethanol Singly and in Combination Against Gram-negative Bacteria," 215 Mibrobio 70:215-229 (1992).

"Fraicheur de Peau Fresh Skin Body Mist," International Product Alert, No. 9, vol. 14, May 5, 1997.

Garcia et al., 2003, "Virucidal activity of essential oils from aromatic plants of San Luis, Argentina." Phytother. Res. 17(9):1073-1075.

Goren et al., 2003, "Analysis of essential oil of *Coridothymus capitatus* (L.) and its antibacterial and antifungal activity." Z. Naturforsch. 58(9-10):687-690.

Hajhashemi et al., 2003, "Anti-inflammatory and analgesic properties of the leaf extracts and essential oil of *Lavandula angustifolia* Mill." Ethnopharmacol. 89(1 ):67-71.

Happi, Household & Personal Products Industry: New ingredients galore at SCC supplier's day, Chemical Business Newsbase, Aug. 1, 2000.

Heard, D,D., and Ashworth, R.W., "The Colloidal Properties of Chlorhexidine and its Interaction with Some Macromolecules," J. Pharm. Pharmac. 20:505-12, 1968.

Larsen et al., 2001 "Fragrance contact dermatitis: a worldwide multicenter investigation (Part II)" Contact Dermatitis 44:344-346.

Lawless, Julia. The Illustrated Encyclopedia of Essential Oils: The Complete Guide to the Use of Oils in Aromatherapy and Herbalism. Element Books, 1995, USA. pp. 132,162-164,169,223,227 and 228.

Lawrence, J.C. et al., "Evaluation of Phenoxeotol—Chlorhexidine Cream as a Prophylactic Antibacterial Agent in Burns," The Lancet, pp. 1037-1040, May 8, 1992.

Manufacturing Chemist: Japan approve Schulke & Mayr's Sensiva SC 50, Chemical Business Newsbase, Jul. 14, 2000.

Minami et al., 2003, "The inhibitory effect of essential oils on herpes simplex virus type-1 replication in vitro." Microbial Immunol. 47(a):681-684.

Modak S, et al., "Rapid Inactivation of Infections Pathogess by Chlorhexidine Coated Gloves," Infection Control and Hospital Epidemiology, 13:463-471, (1992).

Molnycke Healthcare "Hibiclens Antiseptic/Antimicrobial Skin Cleanser" Nov. 10, 2006.

Nair, 2001, "Final report on the safety assessment of Mentha Piperita (Peppermint) oil, Mentha Piperita (Peppermint) Leaf extract, Mentha Piperita (Peppermint) leaf and Mentha Piperita (Peppermint) water," International Journal of Toxicology 20 (SuppI3):61-73.

Paranagama et al., 2003, "Fungicidal and anti-aflatoxigenic effects of the essential oil of *Cymbopogon citratus* (DC.) Stapf. (lemongrass) against *Aspergillus flavus* Linle isolated from stored rice." Lett. Appl. Microbiol. 37(1):86-90.

Parfums, Cosmetiques, Aromes: Japan approves sale of new cosmetics ingredient, Chemical Business Newsbase, Jan. 16, 2001.

Physicians Desk Reference—39th Edition, 1985, p. 1858, Lotrisone.

Physicians Desk Reference—39th Edition, 1985, pp. 2037-2038, chlorhexidine.

Physicians Desk Reference—40th Edition, 1986, pp. 1781-1782, chlorhexidine.

Pfizer "Purell Instant Hand Sanitizer, Product Description" Nov. 10, 2006.

Prevacare:Antimicrobial Hand Gel product description, Johnson & Johnson, Advanced Wound Care, 2001.

Prevcare: Total solution skin care spray product description, Johnson & Johnson, Advanced Wound Care, 2001.

Robinson, K. "Heat beating technology; deodorant market," Soap Perfumery and Cosmetics, v. 69 No. 7 p. 34, Jul. 1996.

Rubbo et al., A Review of Sterilization and Disinfection, Year Book Medical Publishers, Chicago, 161-162 (1965).

S &M in Japan—Schulke & Mayr's Sensiva SC 50 deodorant active ingredient received approval for use in the Japanese market, SPC Asia No. 21, p. 35, May 2000.

Schmolka, I.R., "The Synergistic Effects of Nonionic Surfactants Upon Cationic Germicidal Agents," J. Soc. Cosmet. Chem., 24;577-592, 1973.

Schuhmacher et al., 2003, "Virucidal effect of peppermint oil on the enveloped viruses herpes simplex virus type 1 and type 2 in vitro." Phytomedicine 10:504-510.

Schwarzkopf cares, European Cosmetic Markets, No. 5, vol. 13, May 1, 1996.

Schwarzkopf: Moving into a new era, European Cosmetic Markets, Sep. 1, 1996.

Sensiva SC 50 product description from manufacturer website (www.schuelkemayr.com), Schulke & Mayr, manufacturer, printed Apr. 4, 2001.

Shin, 2003, "Anti-Aspergillus activities of plant essential oils and their combination effects with ketoconazole or amphotericin B." Arch. Pharm. Res. 26(5):389-393.

Silva et al., 2003, "Analgesic and anti-inflammatory effects of essential oils of Eucalyptus." Ethnopharmacoi. 89(2-3);277-283.

SPC, Soap Perfumery and Cosmetics: New for deodorants: Sensiva SC 50, Chemical Business Newsbase, Aug. 12, 1999.

Sugiura., 2000, "Results of patch testing with lavender oils in Japan" Contact Dermatitis 43: 157-160.

Valero and Salmera, 2003, "Antibacterial activity of 11 essential oils against *Bacillus cereus* in tyndallized carrot broth." Int. Food Microbiol. 85(1-2): 73-81.

Velluti et al., 2003, "Inhibitory effect of cinnamon, clove, lemongrass, oregano and palmarose essential oils on growth and fumonisin B1 production by *Fusarium proliferatum* in maize grain." Int. Food Microbiol. 89: 145-154.

Vichy launches oil-free moisturizer, Chemist & Druggist, p. 792, Jun. 8, 1996.

Vilaplana et al., 2002, "Contact dermatitis from the essential oil of tangerine in fragrances" Contact Dermatitis 46: 108.

Wohrl S, Hemmer W, Focke M, Gotz M, Jarisch R. "The significance of fragrance mix, balsam of Peru, colophony and propolis as screening tools in the detection of fragrance allergy." British Journal of Dermatology 2001; 145(2):268-273.

Woodruff,l. "Mixed feelings," Soap Perfumery & Cosmetics, No. 9, vol. 73, p. 39, Sep. 1, 2000.

Aiko Tanaka et al. "Effect of Various Types of Disinfectants on Skin Physiological Function." J. Nursing Science. Toyama Medical and Pharmaceutical University. 1999, vol. 2 pp. 49-58.

U.S. Appl. No. 12/715,026, filed Mar. 1, 2010.

U.S. Appl. No. 10/622,272, Apr. 21, 2010 Response to Non-Final Office Action.

U.S. Appl. No. 10/785,207, Jan. 29, 2010 Supplemental Response to Office Action.

U.S. Appl. No. 10/785,207, May 13, 2010 Final Office Action.

U.S. Appl. No. 10/786,681, Feb. 24, 2010 Response to Final Office Action.

U.S. Appl. No. 10/786,681, Mar. 30, 2010 Non-Final Office Action.

U.S. Appl. No. 11/327,677, Feb. 23, 2010 Notice of Allowance.

U.S. Appl. No. 11/327,677, Apr. 16, 2010 Amendment after Notice of Allowance.

U.S. Appl. No. 11/327,677, May 10, 2010 Notice of Allowance.

U.S. Appl. No. 11/327,677, May 13, 2010 Response to Amendment under Rule 312.

U.S. Appl. No. 11/446,347, Feb. 26, 2010 Response to Non-Final Office Action.

U.S. Appl. No. 11/446,347, Mar. 15, 2010 Notice of Allowance.

U.S. Appl. No. 11/446,347, May 18, 2010 Amendment after Notice of Allowance.

U.S. Appl. No. 11/446,347, Jun. 2, 2010 Response to Amendment after Notice of Allowance.

U.S. Appl. No. 10/891,624, Mar. 5, 2010 Non-Final Office Action.

U.S. Appl. No. 10/891,624, Jun. 4, 2010 Response to Non-Final Office Action.

U.S. Appl. No. 10/622,272, filed Oct. 21, 2010 Response to Non-Final Office Action.

U.S. Appl. No. 12,715,026, filed Nov. 16, 2010 Non-Final Office Action.

* cited by examiner

ZINC SALT COMPOSITIONS FOR THE PREVENTION OF DERMAL AND MUCOSAL IRRITATION

CROSS REFERENCE TO RELATED APPLICATIONS

The present invention is a continuation-in-part of U.S. patent application Ser. No. 10/622,272 filed Jul. 17, 2003, which is a continuation-in-part of pending International Patent Application PCT/US03/03896 filed Feb. 7, 2003, published in English as WO03/066001 on Aug. 14, 2003, which claimed priority to provisional U.S. Patent Application Ser. No. 60/355,549 filed Feb. 7, 2002, the contents of which are incorporated herein by reference in their entireties.

1. INTRODUCTION

The present invention relates to methods and compositions which employ low concentrations of combinations of zinc salts to prevent the irritation of skin or mucous membranes that may be caused by therapeutic agents, by personal hygiene products, or by various physical, chemical, mechanical, or biological irritants, including infectious agents.

2. BACKGROUND OF THE INVENTION

The Center for Disease Control (CDC) estimates that hospital-acquired infections cost the U.S. healthcare system $4.5 billion a year, and that 80% of these infections are transmitted by direct touch. Although the simple use of soap before and after direct contact with a patient can reduce the transmission of these infections, health care workers often fail to employ this simple measure for several reasons. First, washing with soap and water takes time. Second, such washing necessitates the use of running water, sinks, paper towels and other infrastructural needs that are expensive to provide and maintain and therefore not always immediately accessible by health-care personnel. Thus, most health care workers follow the existing washing guidelines only about 50% of the time.

In response to this problem, the CDC recently issued new hand hygiene guidelines for health care workers. One recommendation is for doctors, nurses and other health care workers to use alcohol-based hand antiseptics rather than traditional water-based soaps to decontaminate their hands between contact with each patient to prevent the spread of infections. This new CDC guideline is expected to reduce the time spent to decontaminate hands and hence increase compliance among health-care workers. Moreover, the recommended alcohol-based products can be carried with the health care worker or installed in several convenient places near patient rooms. The alcohol in the lotion will kill the bacteria, and added emollients should keep the hands soft. Furthermore, the product dries on the hands, so running water, sinks, paper towels, etc. are largely unnecessary.

A product called Avagard™, made by 3M, is commercially available having a combination of emulsifiers, namely Beheneth-10, behenyl alcohol, cetylpalmitate, and diisopropyl dimer dilinoleate with 1% chlorhexidine gluconate solution and 61% ethyl alcohol (w/w).

A product called Prevacare™, made by Johnson & Johnson, is commercially available having 60% ethanol as its active ingredient, water as a vehicle, liposome-building blocks including glycerol distearate, stearate-10, cholesterol, and polysorbate 80, sodium laureth sulfate as a surfactant, propylene glycol as a moisturizer, and preservatives including diazolidinyl urea, methylparaben, and propylparaben. Prevacare-D™ is a commercially available product having 60% ethanol as its active ingredient, and also includes cyclomethicone as an emollient, polyethylene and silica as viscosity builders, mineral oil as a moisturizer/emollient, propylparaben as a preservative and fragrance.

A principal drawback with the increased use of alcohol-based products such as Avagard™, Prevacare™, or others presently available or embodied in various issued U.S. or European patents (see e.g. U.S. Pat. Nos. 3,485,915, 4,478,853, 4,956,170, 5,403,864, 5,516,510, 5,776,430, 5,885,562, 5,951,993, 6,022,551, 6,107, 261, 6,136,771, 6,204,230, 6,352,701, and European Patent Application 0604 848) is that certain ingredients in the formulations, including the alcohol itself, may cause irritation and allergic reactions on the skin. This drawback was readily apparent in a recent study of alcohol-based disinfectants among nurses, which showed that adverse reactions occurred in approximately 12% of all individuals following exposure to these products (Cimiotti et al., 2003, Am. J. Infect. Control 31:43-48.). The instant invention provides one means of overcoming this problem. Certain zinc salts may be added to alcohol-based gels, hand scrubs or other products to prevent the irritation that may otherwise be caused by the alcohol or other active or inactive ingredients that they may contain (see e.g. U.S. Pat. Nos. 5,965,610 and 5,985,918, the contents of which are incorporated by reference herein).

Transmission of infectious diseases is also a serious public health concern outside of the health care setting. For example, a growing number of infectious agents may be transmitted by sexual contact, and public health experts increasingly advocate the use of various devices or substances to reduce or prevent the transmission of infectious agents during sexual contact. Unfortunately, such devices or substances often contain irritating components or ingredients that may cause irritation or the dermis or mucous membranes, thereby actually increasing the risk of infection. For example, male or female condoms are often made from latex or other potentially irritating substances. Genital creams, lotions or ointments often contain potentially irritating microbicides, fungicides or spermicides.

In the present invention, specific combinations of two or more water-soluble organic salts of zinc have been identified that are effective in preventing irritation caused by spermicides, microbicides, and alcohol-based gels at concentrations that are low enough so that the risk of zinc toxicity, inactivation of therapeutic compounds, and dermal and/or mucosal irritation are minimized.

It is well known that zinc salts exert numerous biological effects. For example, zinc is essential for normal growth and cognitive development in mammals, and zinc deficiency has been implicated in a host of pathophysiological states in humans, including cognitive impairment, ocular dysfunction, eating disorders and immune dysfunction among many others.

Considering the myriad effects of zinc in humans, it is unlikely that a single mechanism could account for them all. However, one of the most important functions of zinc in vivo may be as a part of metalloproteins known as "zinc finger" proteins. Zinc finger proteins contain cysteine- and/or histidine-rich domains comprised of an α helix and two β strands in an antiparallel orientation that are held together electrostatically by a divalent zinc cation ($Zn^{2+}$). Zinc finger domains are commonly found on proteins that bind to and interact with RNA or DNA. Because zinc finger proteins are essential regulators of cell proliferation, it is easy to understand, at least superficially, how zinc could be crucial for normal growth and cognitive development, which requires large amounts of cell growth. This same mechanism may also explain why zinc is required for normal immune function, since rapid proliferation of various cellular elements of the immune system, such as T-cells and/or B-cells, occurs in response to the presentation of foreign antigens.

Zinc may also play a less direct and less specific role in immune function and other biological processes. Proteins are comprised of linear chains of amino acids, some of which are positively-charged, some of which are negatively-charged, and some of which are neutral. When such a linear chain is allowed to move freely in three-dimensions, constrained only by the peptidic linkages between the individual amino acids, complex three-dimensional structures result. Proteins may assume unique shapes that allow them to interact with other proteins having complementary shapes, the so-called "lock-and-key" theory of protein-protein interactions. However, due to the distribution of charged amino acids, proteins may also have unique electrical configurations that can govern their interactions with other complexly-charged protein molecules. Zinc ions, by binding to negatively-charged regions exposed on the surface of proteins, may alter the charge configuration of the protein and prevent subsequent protein-protein interactions. One practical consequence of this phenomenon, for example within the context of immune function, may be the ability of zinc ions to block the binding of viruses or other pathogens to specific receptors on the cell surface, thus preventing infection.

This latter mechanism may account for the known properties of zinc salts as anti-irritants. Irritation of the skin may ensue following the binding, either specific or non-specific, or proteinaceous or non-proteinaceous compounds to the epithelial cells comprising the surface layer of the skin or mucosa. A large number of people are known to exhibit irritant dermatitis when their skin is exposed to various chemicals, antiseptics (chlorhexidine, quaternary ammonium compound and chlorinated phenols), disinfectants such as alcohol, biological fluids (urine), latex gloves etc. Zinc salts may prevent irritation by altering the charge configuration of the irritant, thereby preventing its subsequent binding to the underlying tissue.

A number of U.S. patents relate to the incorporation of zinc salts in various gel compositions to prevent irritation. For example, U.S. Pat. No. 5,708,023 discloses the use of a gel wherein zinc gluconate comprises the sole gelling agent as a method of preventing skin irritation. Antimicrobial agents may also be incorporated into these gels. However, the relatively high concentrations of zinc (10% to 50% by weight) found in these gels makes them less desirable for internal use, where the diffusion of the water-soluble zinc salt creates the potential for systemic zinc toxicity, which can be manifested as emesis, irritation and corrosion of the gastrointestinal tract, acute renal tubular necrosis and interstitial nephritis.

U.S. Pat. Nos. 5,965,610 and 6,037,386, both entitled "Composition for inactivating irritants in fluids," also disclose compositions containing water-soluble zinc salts such as zinc gluconate, zinc acetate, zinc sulfate, zinc undecylinate and zinc salicylate for use as anti-irritants. When used at high concentrations, these zinc salts can largely prevent irritant dermatitis. Again, these compositions are less suited to internal use due to their relatively high concentrations of zinc (2% or more of zinc oxide or other zinc salts).

U.S. Pat. No. 5,985,918, entitled "Zinc-based anti-irritant creams," relates the use of organic salts of zinc in anti-irritant creams. In the compositions disclosed in this patent, at least 1% and more preferably 5% or more of zinc salts were needed for the products to be completely effective as anti-irritants.

Apart from the potential for systemic zinc toxicity following the absorption of high concentration water-soluble zinc salts through the skin or mucosa following their use in topical creams or gels, zinc itself may be an irritant at high concentrations. Thus, there is a practical upper limit to the amount of zinc that may be contained within anti-irritant creams and lubricants, especially those designed for internal use. The existence of a practical upper limit on the amount of zinc that is desirable for incorporation into contraceptive or antiseptic creams is further evident from the fact that, through its ability to bind to and subsequently inactivate potential irritants such as the contraceptive or antiseptic agent, the inclusion of high concentrations of zinc salts in these products may render them ineffective for their intended functions.

U.S. Pat. No. 5,980,477 of Kelly, entitled "Genital lubricants with zinc salts as anti-viral additives," relates to the incorporation of water-soluble, organic salts of zinc, at concentrations ranging from 0.5%-30%, into genital lubricants or other similar products to effectuate the inactivation of HIV-1 or other viruses implicated in the spread of sexually-transmitted diseases. At the upper limit of the zinc concentration range, there may be an increased risk of zinc toxicity, as well as the potential for vaginal irritation caused by the direct irritant effects of zinc. The effectiveness of the contraceptive agents also may be compromised. Furthermore, Kelly does not appreciate or describe the beneficial anti-irritant effects of low concentrations of combinations of water-soluble, organic salts of zinc.

In the present invention, specific combinations of two or more water-soluble organic salts of zinc have been identified that are effective in preventing irritation caused by spermicides, microbicides, and alcohol-based gels at concentrations that are low enough so that the risk of zinc toxicity, inactivation of therapeutic compounds, and mucosal irritation are minimized. The incorporation of zinc salt combinations into contraceptive or antiseptic lubricants or creams will thus render these products less irritating to the underlying mucosa, and therefore better able to protect against the contraction of infectious diseases, while maintaining the effectiveness of these products for their intended use.

3. SUMMARY OF THE INVENTION

The present invention relates to combinations of water-soluble zinc salts which, when intermixed with gels, creams, lotions or ointments that are then applied to the skin or other surface, can minimize or prevent irritation to the skin. When added to water- or alcohol-based topical disinfectants, the anti-irritant properties of the zinc salts described herein may increase the use of topical disinfectants containing zinc salts among health care workers, thereby reducing the transmission of infectious diseases in hospital settings. These same zinc salt combinations may be added to gels, creams or lubricants containing spermicides, microbicides, fungicides or other potentially-irritating therapeutic agents, to reduce or prevent the irritation of skin or mucosal membranes caused by these therapeutic agents. When employed in genital lubricants, the reduction in irritation of the vaginal mucosa may assist in minimizing the spread of sexually-transmitted diseases.

The invention is based, at least in part, on the following two discoveries. First, the addition of combinations of low concentrations of water-soluble organic salts of zinc to gels, creams, lotions or ointments applied topically were found to increase the ability of these products to prevent irritants from achieving contact with the underlying skin, thus reducing irritation. Second, the addition of combinations of low concentrations of water-soluble organic zinc salts to genital lubricants were observed to reduce the irritation of mucous membranes caused by the presence of potentially-irritating substances such as spermicides, microbicides, fungicides or other therapeutic agents within the lubricant. Preferred embodiments of the invention include topical antimicrobial compositions that lack conventional antibiotics or preservatives, wherein the antimicrobial benefit is created by essential oils (or their active ingredients), emollient solvents and, in some instances, anti-inflammatory agents.

4. DETAILED DESCRIPTION OF THE INVENTION

The present invention relates, at least in part, to methods and compositions for the prevention of the irritation of skin or mucosal surfaces that may occur as a result of exposure to irritant substances. It is based, at least in part, on the discovery that the addition of combinations of water-soluble, organic salts of zinc to gels, creams, lotions, or ointments can increase the ability of these gels, creams, lotions or ointments to prevent irritants from causing irritation of the underlying substrate. While it had been found previously that high concentrations of zinc salts added to gels, creams, lotions or ointments may enhance the protective effects of these products, zinc itself at high concentrations has been shown to produce irritation. Furthermore, high concentrations of zinc ions in these products also raise the potential for local or systemic zinc toxicity in subjects who use these products. One surprising aspect of the instant invention, therefore, is the finding that low concentrations of zinc salts, especially when two or more such salts are used in combination, can achieve a satisfactory degree of anti-irritant effect while minimizing the potential for both zinc-induced irritation and toxicity. A further advantage of the present approach is that the concentrations of the combination of zinc salts advocated in the present invention are sufficiently low so that their addition to gels, creams, lotions or ointments containing biologically-active agents such as spermicides, microbicides, fungicides or other potentially-irritating therapeutic compounds may not be expected to result in the inactivation of these compounds, thereby permitting their use as anti-irritant agents in gels, creams, lotions or ointments containing these compounds.

Accordingly, in various embodiments, the present invention provides for anti-irritant gels, creams, lotions or ointments comprising low concentrations of two or more water-soluble, organic salts of zinc that are effective in preventing or reducing irritation.

The term "low concentration" means percentages of free zinc ions ($Zn^{2+}$) in the gel, cream, lotion or ointment at less than 0.5% on a weight to weight (w/w) basis.

Suitable zinc salts for use in these compositions include zinc acetate (molar solubility in water of 1.64 moles/l), zinc butyrate (molar solubility in water of 0.4 moles/l), zinc citrate (molar solubility in water of <0.1 moles/l), zinc gluconate (molar solubility in water of 0.28 moles/l), zinc glycerate (moderately water soluble), zinc glycolate (moderately water soluble), zinc formate (molar solubility in water of 0.33 moles/l), zinc lactate (molar solubility in water of 0.17 moles/l), zinc picolinate (moderately water soluble), zinc proprionate (molar solubility in water of 1.51 moles/l), zinc salicylate (low water solubility), zinc tartrate (moderately water soluble) and zinc undecylenate (moderately water soluble).

The terms "prevention" or "reduction" of irritation means a decrease in objective or subjective signs of irritation in tissues treated with the gels, creams, lotions or ointments comprising low concentrations of two or more water-soluble, organic salts of zinc of at least 50%, and more preferably by greater than 90% relative to control tissues exposed to the irritant agent and the same gels, creams, lotions or ointments lacking zinc salts. Irritation in this context may be evidenced by redness or other changes in coloration, inflammation or swelling, hypersensitivity, the occurrence of burning, itching or other painful stimuli, or other macroscopic or microscopic changes known to those of ordinary skill in the art to be associated with irritation.

The formulations of the invention (which include, but are not limited to, gels, creams, lotions, lubricants, elixirs, oils, emulsions, ointments, soaps, scrubs, liquids, pastes and the like) may be applied topically to the skin or to the various mucous membranes of the body, including but not limited to those of the oral, nasal, vaginal or rectal cavities, to prevent the effects of exogenous irritants upon these surfaces.

In preferred embodiments, the gel or cream comprises a mixture of water, a gelling agent, a thickening agent, a hydrophilic or hydrophobic polymer, an emulsifying agent, and an emollient. The zinc salts comprise a combination of effective amounts of two or more of the following: zinc acetate (0.1-2.0%), zinc citrate (0.1-2.0%), zinc gluconate (0.1-2.0%) and zinc lactate (0.1-2.0%). In preferred embodiments, the zinc salts are 1% zinc gluconate, 0.2% or 0.4% zinc acetate and 0.2% of either zinc lactate or zinc citrate.

In alternative embodiments, the gel comprises a mixture of water (10-50%), alcohol (30-90%), a zinc gel (a combination of quaternary cationic hydroxy ethyl cellulose (0.1-0.3%) and triple zinc salt mixture containing zinc gluconate (0.1-2.0%), zinc acetate (0.1-2.0%) and zinc lactate (0.05-2.0%)) and emollients (0.3-1%).

In further embodiments, the cream comprises a mixture of water (10-50%), petroleum jelly (10-40%), crothix (0.5-3%), allantoin (0.3-1.0%), salicylic acid (1.0-4.0%), dimethicone (0.5-5.0%), zinc stearate (1.0-5.0%), zinc oxide (0.5-5.0%), a triple zinc salt mixture containing zinc gluconate (0.1-2.0%), zinc acetate (0.1-2.0%) and zinc lactate (0.05-2.0%), and other emollients (10-30%).

In further embodiments, the lotion comprises a mixture of water (60-80%), petroleum jelly (2-10.0%), crothix (0.5-2.0%), crodomol MM (0.5-2.01%), cremerol (0.5-2.0%), zinc stearate (1.0-5.0%), zinc oxide (0.1-3.0%), a triple zinc salt mixture containing zinc gluconate (0.05-2.0%), zinc acetate (0.05-2.0%) and zinc lactate (0.05-2.0%), and emollients (10-30%). In preferred embodiments, the zinc salts are 0.3% zinc gluconate, 0.1 % zinc acetate and 0.1 % of zinc lactate The present invention further relates to hydroalcoholic gel compositions comprising combinations of 1% or less of hydrogel dissolved in water at ambient temperature and 3% or less of emollient dissolved in alcohol or 3% or less of emulsifier wherein said compositions have viscosities below 4000 centipoise (cps) at between 20-40° C. These percentages and further percentages discussing these hydroalcoholic gel compositions should be considered weight/weight percentages, unless otherwise specified. In preferred embodiments of the invention such compositions comprise 30-80% alcohol, 15-70% water, 0.05-0.5% hydrogel, and 0.2-3.0% emollient and/or 0.05-0.5% emulsifier with viscosities of less than 2000 cps, most preferably between 50-500 cps. Additional embodiments of this invention further include silicone polymer, emollient solvent, antimicrobial agent, and thickening agent, while maintaining the low viscosities as preferred.

Various embodiments of the invention may comprise an emollient, such as, but not limited to, PEG 20 almond glycerides, Probutyl DB-10, Glucam P-20, Glucam E-10, Glucam P-10, Glucam E-20, Glucam P-20 distearate, glycerin, propylene glycol, cetyl acetate, and acetylated lanolin alcohol, cetyl ether, myristyril ether, hydroxylated milk glycerides, polyquaternium compounds, copolymers of dimethyl dialyl ammonium chloride and acrylic acid, dipropylene glycol methyl ethers, polypropylene glycol ethers and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter. Preferred emollient solvents of the invention include octoxyglycerin (Sensiva®), pentylene glycol, 1,2 hexanediol and caprylyl glycol.

Various embodiments of the invention may comprise a stabilizing agent, such as, but not limited to, an antioxidant (which may be at a concentration of 0.2-1%), such as but not limited to vitamin C (ascorbic acid) or vitamin E (tocopherol).

Various embodiments of the invention may comprise a surfactant (which may be at a concentration of 0.2-1.0%), such as but not limited to incromide or silicone-based surfactants (Masil SF-19, BASF). The stabilizing agents surprisingly appear to remove the turbidity of the gel, cream, lotion or ointment, resulting in a clear product that imparts a light feel to the surface to which it is applied.

Various embodiments of the invention may comprise a thickening agent, such as but not limited to the following (at a preferred concentration of 0.6-2%): stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, or an emulsifying wax such as but not limited to Incroquat and Polawax. Other thickening and/or gelling agents suitable for incorporation into the anti-irritant gels, creams, lotions or ointments described herein include, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, crodomol, crothix, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

An embodiment of the invention may comprise phenoxyethanol (0.3-1.0%) as a solubilizing agent.

Various embodiments of the invention may comprise a humectant, such as but not limited to glycerin, 1-2-propylene glycol, dipropylene glycol, polyethylene glycol, 1,3-butylene glycol, or 1,2,6-hexanetriol.

Various embodiments of the invention may comprise one or more antimicrobial or preservative agent, preferably at a concentration between 0.05 and 2%. Examples of preferred antimicrobial and/or preservative agents include, but are not limited to, chlorhexidine gluconate (CHG), benzalkonium chloride (BZK), or iodopropynylbutyl carbamate (IPBC; Germall plus). Further examples of antimicrobial agents include, but are not limited to, iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzalkonium chloride, dequalinium chloride, biguanides such as chlorhexidine (including free base and salts (see below)), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylenol, foscarnet, miconazole, fluconazole, itriconazole, ketoconazole, and pharmaceutically acceptable salts thereof.

Pharmaceutically acceptable chlorhexidine salts that may be used as antimicrobial agents according to the invention include, but are not limited to, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-a-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Chlorhexidine free base is a further example of an antimicrobial agent.

These and further examples of antimicrobial agents useful in this invention can be found in such references as Goodman and Gilman's The Pharmacological Basis of Therapeutics (Goodman Gilman A, Rall T W, Nies A S, Taylor P, ed. (Pergamon Press; Elmsford, N.Y.: 1990)), the contents of which are hereby incorporated by reference.

In one preferred embodiment, a composition of the invention comprises 1% chlorhexidine and a combination of at least two or more of the following: zinc acetate (0.1-2.0%), zinc citrate (0.1-2.0%), zinc gluconate (0.1-2.0%) and zinc lactate (0.1-2.0%). In another preferred embodiment, a composition of the invention comprises 2% miconazole and a combination of at least two or more of the following: zinc acetate (0.1-2.0%), zinc citrate (0.1-2.0%), zinc gluconate (0.1-2.0%) and zinc lactate (0.1-2.0%).

Various embodiments of the invention may comprise a neutralizing agent to neutralize carboxyl groups present in one or more other component, such as carboxyl groups in a thickening agent. Suitable neutralizing agents include diisopropylamine and triethanolamine.

Various embodiments of the invention may comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5-2.0%. Suitable concentrations of surfactant are between about 0.05% and 2%.

Water used in the formulations described herein is preferably deionized water having a neutral pH. When used in hydroalcoholic gel compositions, the concentration of water should be suitable to dissolve the hydrogels according to the invention.

Various embodiments of the invention may comprise additional additives, including but not limited to a silicone fluid (such as dimethicone or cyclomethicone), dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

Various embodiments of the invention may comprise an essential oil ("EO"), which is a volatile oil obtained from a plant or an animal source that comprises one or more active agent (also referred to herein as an Isolated Component or "IC") which may be, for example but not by way of limitation, a monoterpene or sesquiterpene hydrocarbon, alcohol, ester, ether, aldehyde, ketone, or oxide. Examples of these EOs include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, and tangerine oil. Alternatively, the present invention provides for the use of active agents found in essential oils (ICs) such as, but not limited to, 1-citronellol, α-amylcinnamaldehyde, lyral, geraniol, farnesol, hydroxycitronellal, isoeugenol, eugenol, eucalyptus oil and eucalyptol, lemon oil, linalool, and citral. Apart from their effects as fragrances or flavorants, such compounds also may be useful in the instant invention as antimicrobial agents.

A hydrogel, as used herein, may comprise hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), or chitosan pyrrolidone carboxylate (Kytomer PC). These hydrogels preferably do not adversely bind to any added antimicrobial agent, therefore leaving the optionally added antimicrobial agent free for rapid and long-term activity. In addition, it has been discovered that alcohol used to form the hydroalcoholic gel is not trapped in the hydroalcoholic gel composition and is therefore available for rapid and long-term action. The hydrogel may be present in a concentration between 0.1-1.0%, and preferably is a cationic hydroxyethyl cellulose (U-care polymers) in a concentration between 0.05-0.5%, most preferably 0.2%.

In hydroalcoholic gel compositions of the invention, alcohols that may be used include aliphatic alcohols, including, but not limited to, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol. The concentration of alcohol may be between 30% and 95%, preferably between 40% and 70%; preferably the aliphatic alcohols is ethanol or isopropyl alcohol at a concentration between and 60% and 95%. When present, the concentration of fatty alcohols is preferably between 0.5% and 5.0%; and, when present, the concentration of hexanol is preferably between 3% and 10%, more preferably 5%.

Hydroalcoholic gel compositions of the invention may optionally comprise an emollient and/or humectant such as the emollients and humectants discussed above, preferably one or more of PEG 20 Almond Glycerides, Probutyl DB-10, Glucam P20, Glucam E-10, Glucam P-10, Glucam E-20, Glucam P-20 distearate, glycerin, propylene glycol, octoxyglycerin (Sensiva®), cetyl acetate and acetylated lanolin alcohol (Acetulan), cetyl ether (PPG-10), myristyl ether (PPG-3), hydroxylated milk glycerides (Cremerol HMG), polyquatemium compounds (U-care compounds), chitosan (Kytamer), copolymer of dimethyl dialyl ammonium chloride and acrylic acid (Merquat), dipropylene glycol methyl ethers (Dowanol DPM Dow Coming), or polypropylene glycol ethers (Ucon 50-HB-660, Union Carbide). Preferably the emollient is present at a concentration of 3% or less, such that the viscosity of the composition is preferably less than 2000 centipoise at 20-40° C., more preferably between 0.2 and 3%.

Hydroalcoholic gel compositions of the invention may optionally comprise a surfactant and/or emulsifier, such as the emulsifiers and surfactants discussed above, and preferably a non-ionic or cationic self-emulsifying wax that is soluble in alcohol at ambient temperature. Suitable surfactant/emulsifiers include but are not limited to Incroquat Behenyl TMS, Incroquat Behenyl TMS-50, Polawax, stearyl alcohol and cetearyl alcohol. These emulsifiers may be present at a concentration between 0.05-3.0%. Preferred emulsifiers include Incroquat Behenyl TMS, which is a mild cationic emulsifier as well as an excellent conditioner, and Polawax, which is a non-ionic self emulsifying wax, individually at a concentration of between 0.05-0.5%, and in combination at a concentration of between 0.05-0.5%, more preferably in combination at a concentration ratio of approximately 1:1. If more than one emulsifier is used, it is preferred that the total concentration of emulsifiers present is between 0.05-0.5%.

A hydroalcoholic gel of the invention may optionally comprise a silicone polymer such as, but not limited to, one or more than one polydimethylsiloxane polymer (Dow Coming 225 Silicone Fluid), dimethiconol fluid in dimethicone (Dow Coming 1403 Silicone Fluid), cyclomethicone and dimethicone copolyl (Dow Coming 3225C Silicone Fluid), or silicone glycol (BASF 1066 DCG polyol). Preferred concentrations of silicone polymer are between about 0.1-1.0%.

A hydroalcoholic gel of the invention may optionally comprise an emollient solvent such as, but are not limited to, those listed above or one or more than one glycidyl ethers having alkyl chains up to and including 18 carbon molecules and ethoxylates and propoxylates thereof, glyceryl ethers having alkyl chains up to and including 18 carbon molecules and ethoxylates and propoxylates thereof, mono- and diglyceryl ethers having alkyl chains up to and including 18 carbon molecules and ethoxylates and propoxylates thereof, ethoxylate and propoxylate ethers, ethoxy diglycol esters, ethyl hexyl alcohol propoxylate, propylene glycol esther ethoxylates or propoxylates, or, preferably Arlamol (Altas). Preferred concentrations of emollient solvent are between 0.5-5%.

A hydroalcoholic gel of the invention may optionally comprise a thickening agent, such as, but not limited to, a thickening and/or gelling agent discussed above, preferably behenyl alcohol, crodomol, or crothix. Preferred concentrations of thickening agent are between 0.05-10%. Gelling agents such as Caropol are not preferred due to their high viscosity and their requiring neutralizing agents to neutralize the gelling agent with alkaline materials.

A hydroalcoholic gel of the invention may optionally comprise one or more antimicrobial agent, such as those set forth above. Preferably, the concentration of the one or more than one antimicrobial agent is less than 3%. In particular non-limiting embodiments of the invention, hydroalcoholic gels may comprise chlorhexidine gluconate, benzalkonium chloride and phenoxyethanol, preferably at a concentration of between 0.05-0.5%, 0.1-0.25%, and 0.1-1.0%, respectively. Because cationic antimicrobials, such as biguanides and quaternary ammonium compounds, can bind to the surface of the skin, they may not be available to inactivate pathogens that come into contact with the skin. The gel formulation according to the invention preferably forms a film on the surface of the hand when applied, which film acts as a barrier preventing the antimicrobial agents that may be added to the gel from binding to the surface of the skin.

Ambient temperature is defined herein between 20 and 35° C. Room temperature is defined herein between 20 and 25° C.

The present invention further provides for spermicidal gels, creams, lubricants, lotions or ointments containing low concentrations of two or more water-soluble, organic salts of zinc that are effective in reducing or preventing the irritation caused by the spermicidal agent. Such formulations may be applied topically to the skin or mucosa of the urogenital, perineal area, or to the surface of latex articles such as male or female condoms, to prevent the irritating effects of spermicides that are incorporated into the gel. These products have the additional advantage of minimizing or preventing irritation caused by allergic reaction to latex. Spermicidal agents are well known to those of ordinary skill in the art, and include, but are not limited to, detergent-based spermicides. In a preferred embodiment, the spermicide is nonoxynol-9 and the zinc salts comprise a combination of two or more of the following: zinc acetate (0.1-0.3%), zinc citrate (0.1-0.3%), zinc gluconate (0.1-2.0%) and zinc lactate (0.1-0.3%). In a preferred embodiment, the zinc salts are 0.3% zinc gluconate, 0.1% zinc acetate and 0.1% zinc lactate.

In non-limiting embodiments, a composition of the invention may comprise a pre-existing formulation, such as a commercially available cream, liquid, gel or lotion. Examples of commercially available formulations that may be so used include, but are not limited to, personal lubricants sold under the trade names "KY JELLY," "ASTROGLIDE," and "PRE-VACARE" and lotions sold under the trade names "SOFT-SENSE," "LOTION SOFT," "CUREL," and "KERI". SOFT-SENSE (Johnson & Son, Inc., Racine, Wis.) is known to contain purified water, glycerin USP, distearyldimonium chloride, petrolatum USP, isopropyl palmitate, 1-hexadecanol, tocopheryl acetate (vitamin E USP), dimethicone, titanium dioxide USP, methyl paraben, propyl paraben, sodium chloride, and fragrance. LOTION SOFT (Calgon Vestal, St. Louis, Mo.) is a nonionic moisturizing lotion which is known to contain mucopolysaccharide. CUREL (Bausch & Lomb Incorporated, Rochester, N.Y.) is known to contain deionized water, glycerin, quatemium-5, petrolatum, isopropyl palmitate, 1-hexadecanol, dimethicone, sodium chloride, fragrance, methyl paraben, and propyl paraben.

The invention provides for methods of using the foregoing compositions to prevent irritation to an epithelial tissue (e.g. a mucosal tissue or the skin) comprising applying an effective amount of the composition to the surface. Examples of irritants against which protection may be afforded include, but are not limited to, those induced by physical, chemical, mechanical or biological irritants. Specific examples of the foregoing irritants include, but are not limited to, means for hair removal (e.g. depilatories, waxing and razors), hair relaxants (e.g. sodium hydroxide, calcium hydroxide, thioglycolates), antiperspirants (e.g. aluminum chlorhydrate and other aluminium salts), dermatological treatments (e.g. alpha hydroxy acids (AHAs), especially glycolic and trichloroacetic acids), keratoyltic skin-irritating conditions (e.g. psoriasis, dandruff, etc.), infectious skin irritants (e.g. bacteria and fungi), and agents applied for therapeutic purposes. The epithelial surface to be protected from irritation may be dermal or mucosal, including vaginal, anorectal, oral or nasal.

The invention further provides for methods of protecting against infection comprising applying, to an epithelial tissue such as the skin or a mucous membrane of the body, an effective amount of one of the foregoing compositions which inhibits irritation of the tissue. Examples of infectious agents against which protection may be afforded include, but are not limited to, infectious agents associated with sexually transmitted diseases, including Human Immunodeficiency Virus (HIV), Human Papilloma Virus (HPV), Herpes Simplex Virus (HSV), *Chlamydia trachomatis*, *Neisseria gonorrhoea*, *Trichomonas vaginalis*, and *Candida albicans*, as well as infectious agents that may be encountered in a health care setting, including but not limited to *Staphylococcus aureus*, *Pseudomonas aeruginosa*, *Streptococcus pneumoniae*, *Escherichia coli*, *Salmonella typhimurium*, *Enterococcus*, and *Neisseria meningitidis*, HIV, varicella virus and Hepatitis viruses (e.g., A, B, and C).

In non-limiting embodiments, the present invention provides for a topical composition comprising an antimicrobial composition that comprises an emollient solvent and an essential oil (or active component (IC) thereof). Although such topical compositions may optionally contain additional antimicrobial (including preservative) compounds, in preferred non-limiting embodiments, the antimicrobial composition consists essentially of an emollient solvent and an essential oil (see the following paragraph). Said composition may additionally comprise an anti-inflammatory agent, for example, but not limited to, salicylic acid, acetyl salicylic acid, or zinc salicylate. The topical composition may, or alternatively may not, comprise one or more zinc salt, which may be a water-soluble organic zinc salt such as those listed herein. The present invention further provides for methods for producing an antimicrobial effect on the skin or mucous membrane of a subject using such topical compositions.

In non-limiting embodiments, the topical compositions of the preceding paragraph lack an antimicrobial agent selected from the group consisting of iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzalkonium chloride, dequalinium chloride, biguanides such as chlorhexidine (including free base and salts (see below)), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylenol, foscarnet, miconazole, fluconazole, itriconazole, ketoconazole, and pharmaceutically acceptable salts thereof.

In additional embodiments, the present invention provides for an anti-irritant composition comprising two or more zinc salts at concentrations between 0.1 and 2% and further comprising panthenol at a concentration of between about 0.2-5%. Said composition may optionally further comprise alcohol and/or one or more zinc salt, which may be a water soluble or non-water soluble zinc salt or a combination thereof. Non-limiting examples of non-water soluble zinc salts include zinc oxide and zinc stearate, as well as other zinc salts having equivalent or lower solubilities in water relative to those compounds.

In still further embodiments, the present invention provides for a zinc slurry that may be applied to a latex article (such as a condom or glove) to reduce or prevent irritation. The zinc slurry may comprise, for example but not by way of limitation, two water-soluble zinc salts (as set forth above) as a concentration of between 1-5%, two water-insoluble zinc salts (as set forth above) at a concentration of 2-10%, panthenol at a concentration of 5-40%, and glycerine at a concentration of 20-50%. Such a slurry may be mixed with a liquid, such as a silicone fluid, in a ratio of between 1:5 to 1:10, and then applied to the surface of the article which will be in contact with the skin.

Percentages herein are weight/weight unless specified otherwise.

5. WORKING EXAMPLES

5.1. Example 1

Evaluation of the Anti-Irritant Effect of Various Zinc Salts in a Gel Base as a Barrier to Irritants using Chlorophyllin Dye as the Test Model Chlorophyllin is a dye that stains the skin a deep green color. The stain can only be removed after several washes with soap and water. After application of a gel base (55% Propylene glycol, 44.6% Water, 0.4% Xanthum gum) containing various combinations of zinc salts (Table 1) to the skin of human volunteers, the extent of penetration of externally-applied chlorophyllin dye through the gel formulations was determined.

In these studies, the forearms of the human volunteers were washed with soap and water and then dried. The gel formulation to be tested (0.1 g) was spread over a 4 cm by 4 cm area of the forearm and allowed to dry for 5 minutes. A 3 cm by 3 cm square of paper towel (Marcal™) was dipped in a 1.5% aqueous solution of chlorophyllin and placed centrally on the area of the skin to which the gel had been applied. The site was then covered by plastic wrap which was immobilized via surgical tape placed around its edges.

After 1 hour, the plastic and paper toweling were removed and the forearm was dried with a tissue by rubbing five times. An "anti-irritant" score was assigned based on the degree of coloration of the skin by the dye. The degree of coloration was scored as follows: 0=no color, 1=slight color, 2=moderate color, 3=heavy coloration. The site was then rinsed under lukewarm water while rubbing ten times and a post-wash score was read. After rinsing with soap and water and drying by blotting with dry tissue, the tests areas were scored again. The average of these three scores for each condition is shown in Table 1. From these studies, the combination of 1% zinc gluconate, 0.2% zinc acetate and 0.2% zinc lactate is superior to all single zinc salts and to other zinc salt combinations in preventing the penetration of the dye through the lubricant base and its binding to the surface of the skin.

TABLE 1

Inhibition of Chlorophyllin Penetration by Zinc Salts

| Zinc salts in lubricant base* | Scoring of coloration |
|---|---|
| 2.0% zinc gluconate | 0.5 |
| 1.4% zinc gluconate | 1.0 |
| 0.6% zinc gluconate | 1.0 |
| 1.4% zinc lactate | 1.5 |
| 1.4% zinc acetate | 0.5 |
| 1.4% zinc citrate | 1.0 |
| 1.0% zinc gluconate + 0.4% zinc acetate | 0.5 |
| 1.0% zinc gluconate + 0.2% zinc acetate + 0.2% zinc lactate | 0.1 |
| 1.0% zinc gluconate + 0.2% zinc acetate + 0.2% zinc citrate | 0.3 |
| 0.6% zinc acetate + 0.8% zinc lactate | 1.0 |
| Control (lubricant base only) | 3.5 |

*The necessary amount of lubricant base was added to each sample to achieve 100 g.

5.2. Example 2

Evaluation of the Anti-Irritant Effect of Zinc Salt-Containing Gel-based Lubricant Composition using a Strong Skin Irritant on a Volunteer Methyl salicylate is the active ingredient in Ben-gay™ lotion. This compound is known to be an irritant in certain individuals. A volunteer who exhibits an allergic reaction to methyl salicylate was used as a test subject to evaluate the ability of gel bases containing various zinc salt compositions to prevent methyl salicylate-mediated irritation.

In this study, 10% of Ben-gay™ lotion was mixed with 90% of lubricant (base composition was the same as in Example 1 containing various zinc salt formulations (Table 2) and 0.2 gram per site was applied at three different sites located on the left and right forearms of the volunteer for a total of six sites. After 5 min, the site was wiped with a dry tissue to remove the gel formulation and the degree of irritation was noted. Irritation was defined as the presence of redness, which was scored as follows: 0=no redness, 1=slight redness, 2=moderate redness, 3=heavy redness. The presence of a burning sensation, if any, was also noted. The results of these studies are shown in Table 2.

TABLE 2

Reduction of Skin Irritation by Zinc Salts

| Zinc salt formulation | Scoring of skin reaction (redness) |
|---|---|
| 1% zinc gluconate | 2.5* |
| 0.6% zinc gluconate | 1.5 |
| 0.3% zinc gluconate | 1.0 |
| 1% zinc gluconate + 0.2% zinc acetate | 1.0 |
| 1% zinc gluconate + 0.2% zinc acetate + 0.2% zinc citrate | 0.5 |
| 1% zinc gluconate + 0.4% zinc acetate + 0.2% zinc citrate* | 0.2 |
| 0.4% zinc acetate + 0.2% zinc citrate | 0.5 |
| 0.5% zinc gluconate + 0.1% zinc acetate + 0.1% zinc citrate | 0.5 |
| 0.3% zinc lactate + 0.3% zinc acetate | 1.5 |
| 0/3% zinc gluconate + 0.2% zinc lactate + 0.2% zinc acetate | 0.5 |
| 0.3% zinc gluconate + 0.1% zinc acetate + 0.1% zinc lactate | 0.5 |
| Control (lubricant base only) | 3.0 |

*Burning sensation

Based on these findings, gels incorporating zinc gluconate alone were not able to prevent methyl salicylate-induced irritation, and in fact higher proportions of zinc gluconate may cause some burning sensation independent of the methyl salicylate irritant. In contrast, gels incorporating two or more of the zinc salts consisting of zinc gluconate, zinc acetate, zinc lactate and zinc citrate significantly reduced the irritant effects of methyl salicylate. One of these triple zinc salt compositions (1% zinc gluconate+0.4% zinc acetate+0.2% zinc citrate) reduced the redness induced by the methyl salicylate, but also produced some burning sensation in the volunteer. Interestingly, a gel formulation containing these same three zinc salts but at a lower concentration (0.5% zinc gluconate+0.1% zinc acetate+0.1% zinc citrate) was nearly as effective in preventing the methyl salicylate-induced irritation, but did not cause any burning.

5.3. Example 3

Evaluation of the Anti-Irritant Effect of Zinc Salt-Containing Lubricant Compositions on Nonoxynol-9-induced Irritation of Vaginal Mucosa in a Rabbit Model Nonoxynol-9, when present in gel-based lubricants at 9% w/w, has been shown to be a human irritant. Nonoxynol-9 has also been shown to produce irritation of the vaginal mucosa in a rabbit model. This animal model was used to evaluate the anti-irritant efficacy of various zinc salt compositions in vivo. Due to the limited number of animals available, only a limited number of zinc salt combinations could be tested. Because zinc gluconate has been shown to prevent latex allergies, this salt was tested alone and also in combination with zinc lactate and zinc acetate, which represented one of the better combinations of zinc salts identified in example 2 and still contained an amount of zinc gluconate sufficient to protect against allergic reactions to latex.

In these studies, three groups of rabbits containing six animals each received one of three treatments as indicated in Table 3. The zinc salts indicated in this table were mixed in a lubricant base (base composition was the same as in Example 1) which also contained the spermicidal agent nonoxynol-9 (9% w/w). Two ml of the zinc salt lubricant compositions indicated in Table 3 was instilled into the vagina of each rabbit daily for five consecutive days. At the end of this period, a veterinary pathologist evaluated each animal both macroscopically and microhistopathologically and scored the degree of vaginal irritation that was present. Irritation was quantified as follows: 0=No irritation, 1-4=Minimal Irritant, 5-8=Mild Irritation, 9-11=Moderate Irritation, 12-16=Severe Irritation. The veterinary pathologist indicated that a degree of irritation represented by a score of 3 or less would not be noticeable in humans, while a score of 8 or more would be associated with noticeable irritation in at least some human subjects.

As shown in Table 3, gel-based lubricant containing 9% nonoxynol-9 produces mild to moderate irritation of the vaginal mucosa in rabbits, and this irritation is actually exacerbated by the presence of zinc gluconate (0.3% w/w) alone. In contrast, when this same proportion of zinc gluconate is added together with zinc lactate and zinc acetate, each at 0.1% w/w, the irritating effects of nonoxynol-9 are largely prevented. These findings suggest that this triple zinc salt combination can be used to prevent irritation from spermicides and microbicides, and may also reduce latex-induced irritation when applied on the surface of a latex condom.

TABLE 3

Reduction of Nonoxynol-9-induced Vaginal Mucosal Irritation by Zinc Salts

| Treatment Group | Score (0–16) | | | | | | Average |
|---|---|---|---|---|---|---|---|
| 0.3% zinc gluconate | 2 | 16 | 6 | 16 | 7 | 16 | 10.5 |
| 0.3% zinc gluconate + 0.1% zinc lactate + 0.1% zinc acetate | 3 | 3 | 3 | 4 | 3 | 3 | 3 |
| Negative Control - lubricant base only | 16 | 7 | 7 | 6 | 7 | 6 | 8 |

5.4. Example 4

Evaluation of the Effects of Zinc Salts on the Detergent Actions of Nonoxynol-9

As introduced above, nonoxynol-9 is a spermicidal agent commonly used in genital lubricants. However, this agent is known to cause irritation and abrasions of the vaginal wall, creating the counter-productive risk of higher rates of infection by sexually-transmitted disease-causing pathogens including viruses or bacteria. Zinc salts can be incorporated into nonoxynol-9-containing lubricants to prevent this irritation, but they may also prevent the desired spermicidal effects of this compound. Thus, additional studies were performed to examined which zinc salts, and at what levels, could potentially interfere with the spermicidal effects of nonoxynol-9.

In these studies, the ability of nonoxynol-9 to lyse red blood cells was employed as an indirect indicator of its spermicidal effects. Thus, any composition of zinc salts that prevented the nonoxynol-9-mediated lysis of red blood cells would be likely to prevent the spermicidal effects of this compound and therefore be unsuitable as an anti-irritant in genital lubricants containing this spermicide. Lysis was evaluated be mixing 0.5 ml of a gel base formulation (60% propylene glycol, 40% water and 0.075% hydroxymethyl propyl cellulose (K-100M)) containing 8% nonoxynol-9 and the various combinations of zinc salts shown in Table 4 with 0.5 ml of red blood cells isolated from rats. After five minutes of incubation at 37° C., the mixtures were centrifuged and the resulting supernatants were examined for signs of red blood cell lysis. Lysis was scored as follows: +=100% lysis, ±=50% lysis, −=no lysis.

As shown in Table 4, zinc ion concentrations of 0.28% when introduced as zinc acetate impair the ability of nonoxynol-9 to lyse red blood cells. Interestingly, when the concentration of zinc ions is increased even further (to up to 0.38%) by the incorporation of both zinc gluconate and zinc acetate into the gel, the lytic activity of nonoxynol-9 is maintained. This finding further demonstrates the advantages of combinations of zinc salts over single zinc salts.

TABLE 4

Effect of Zinc Salts on the Detergent Actions of Nonoxynol-9

| Zinc Salt Formulation of Gel | Percentage of Zinc Ions | Lysis |
|---|---|---|
| Negative Control (lubricant base only) | — | − |
| Positive Control (lubricant base plus 8% nonoxynol-9) | — | + |
| 0.8% zinc acetate | 0.28 | − |
| 0.4% zinc acetate | 0.14 | + |
| 2% zinc gluconate | 0.24 | + |
| 2% zinc gluconate + 0.4% zinc acetate | 0.24 + 0.14 (0.38) | + |
| 1% zinc gluconate + 0.4% zinc acetate | 0.12 + 0.14 (0.26) | + |
| 1% zinc gluconate + 0.2% zinc acetate | 0.12 + 0.07 (0.19) | + |
| 0.3% zinc gluconate + 0.2% zinc acetate + 0.2% zinc lactate | 0.045 + 0.07 + 0.05 (0.165) | + |
| 0.3% zinc gluconate + 0.2% zinc acetate + 0.2% zinc citrate | 0.045 + 0.07 + 0.00 (0.115) | + |

The above-described studies suggest that zinc salts may be added to nonoxynol-9-containing lubricants without impairing the detergent activities of the nonoxynol-9. However, the assay of nonoxynol-9-induced lysis employed in these studies was not quantitative. A second study was therefore performed to quantify the effects of the addition of zinc salts on the detergent action of nonoxynol-9.

In these studies, 0.5 ml of lubricant (0.5 ml of PBS in the case of control) is added to 0.5 ml of packed red blood cells. After a five minute incubation at room temperature, the mixture is diluted with 1 ml PBS, mixed and centrifuged. The supernatant (containing the lysed red cells) is diluted 1:100 with PBS. Red cell hemolysis is then quantified by measuring the absorbance of 450 mm wavelength light transmitted by the lysed cell supernatant using a Spectronic-20 spectrophotometer. The high amount of absorbance indicates that a high amount of hemolysis has occurred. A solution containing only PBS is used as a blank reference.

The following two lubricants were compared:

| Lubricant 1 (Lubricant Base Only) | |
|---|---|
| Xanthum gum | 0.3% |
| Water | 44.1% |
| Propylene Glycol | 55% |
| Silicone DC225 | 0.3% |
| Silicone DC1403 | 0.3% |

| Lubricant 2 (Lubricant Base plus Zinc Salts) | |
|---|---|
| Xanthum gum | 0.3% |
| Water | 43.6% |
| Zinc gluconate | 0.3% |
| Zinc acetate | 0.1% |
| Zinc lactate | 0.1% |
| Propylene Glycol | 60% |
| Silicone DC225 | 0.3% |
| Silicone DC 1403 | 0.3% |

TABLE 5

Quantitation of the Effects of Zinc Salts on the Detergent Action of Nonoxynol-9

| Lubricant | Optical Density (O.D. 450) |
|---|---|
| Control (Red Cells + PBS) | 0.22 |
| Lubricant 1 + NN9 (9% w/w) | 0.50 |
| Lubricant 2 + NN9 (9% w/w) | 0.44 |

Although the addition of zinc salts to the lubricant base exerted a slight effect on the ability of nonoxynol-9 to lyse red blood cells, this effect was not statistically significant. Thus, the zinc salt composition containing 0.3% zinc gluconate+0.1% zinc acetate+0.1% zinc lactate does not interfere with the detergent action of NN9, and the same or lower concentrations of zinc salts can be used as an anti-irritant in sexual lubricants and creams of lubricants containing antimicrobial/antiviral agents which are used to prevent STD.

5.5. Example 5

Evaluation of the Effects of Zinc Salts on the Antimicrobial Action of Chlorhexidine Gluconate Chlorhexidine gluconate is a microbicidal agent commonly used in antiseptic gels and creams employed in wound dressing. However, this agent is known to cause irritation in at least some proportion of the human population. Zinc salts may be incorporated into chlorhexidine-containing products to prevent this irritation, but they may also prevent the desired microbicidal effects of this compound. Thus, a series of studies were initiated to examine whether zinc salts interfered with the microbicidal effects of chlorhexidine.

In these studies, the ability of chlorhexidine to inhibit the growth of S. aureus in culture was employed as an indicator of chlorhexidine's microbicidal effects. Briefly, 0.5 ml of a solution containing 1% chlorhexidine gluconate (CHG), 50% ethanol and 50% propylene glycol, plus or minus 2% zinc gluconate, was spread on the surface of a 3 cm×3 cm piece of wound dressing. After drying for one hr, the dressing was subdivided into 1 cm×1 cm pieces and placed on the surface of a Trypticase Soya Agar (TSA) plate seeded with 0.3 ml of S. aureus ($10^8$ colony-forming units (cfu)/ml) The plates were incubated at 37° C. for 24 hr and the zone of inhibition was measured. The results of these studies are shown below in Table 5. The addition of 2% zinc gluconate had no effect on the ability of chlorhexidine to inhibit the growth of S. aureus, indicating that the addition of this concentration of zinc to a gel containing this microbicidal agent did not result in its inactivation.

TABLE 6

Effect of Zinc on the Microbicidal Action of Chlorhexidine

| Treatment | Zone of inhibition (mm) |
| --- | --- |
| Blank (no solution) | 0 |
| Negative Control (CHG solution without zinc) | 14 |
| CHG solution + 2% zinc gluconate | 17 |

5.6. Example 6

Hydroalcoholic Gel Formulations Containing Zinc Salt Complexes

The following alcohol gel formulations containing anti-irritant zinc salt complexes were prepared and some were then evaluated for their rapid and sustained disinfectant activity either in vitro or in two volunteers who have shown irritation and redness following exposure to certain alcohol gels (Prevacare™, Johnson & Johnson).

| | (% By weight) |
| --- | --- |
| ZINC GEL A | |
| Water | 26.63 |
| Ucare (JR 30) | 0.3 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Phenoxyethanol | 0.7 |
| Glycerin | 1.0 |
| Cetyl ether (PPG 10) | 0.5 |
| ZINC GEL B | |
| Water | 26.13 |
| Ucare (JR 30) | 0.3 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Phenoxyethanol | 0.7 |
| Glycerin | 1.0 |
| Cetyl ether (PPG 10) | 0.5 |
| Vitamin C | 0.5 |
| ZINC GEL C | |
| Water | 25.53 |
| Ucare (JR 30) | 0.3 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Klucel | 0.3 |
| Phenoxyethanol | 0.7 |
| Glycerin | 1.0 |
| Cetyl ether (PPG 10) | 0.5 |
| Triclosan | 0.3 |
| Vitamin C (Ascorbic acid) | 0.5 |
| ZINC GEL D | |
| Water | 26.13 |
| Ucare (JR-30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| ZINC GEL D1 | |
| Water | 26.73 |
| Ucare (JR-30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Phenoxyethanol | 0.7 |
| Glycerin | 1.0 |
| Cetyl ether (PPG 10) | 0.5 |

-continued

| | (% By weight) |
|---|---|
| ZINC GEL E | |
| Water | 25.33 |
| Ucare (JR 30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| Cetyl ether (PPG 10) | 0.5 |
| Triclosan | 0.3 |
| Vitamin C | 0.5 |
| ZINC GEL F | |
| Water | 26.08 |
| Ucare (JR30) | 0.2 |
| Zinc gluconate | 0.1 |
| Zinc acetate | 0.1 |
| Zinc lactate | 0.05 |
| Germall plus | 0.2 |
| Chlorhexidine gluconate | 0.05 |
| Benzalkonium chloride | 0.12 |
| Ethanol | 70 |
| Incroquat | 0.6 |
| Phenoxyethanol | 0.7 |
| Glycerin | 1.0 |
| Cetyl ethyl (PPG10) | 0.5 |
| Incromide CAC | 0.3 |
| ZINC GEL G | |
| Water | 26.55 |
| Ucare (JR30) | 0.2 |
| Zinc gluconate | 0.1 |
| Zinc acetate | 0.1 |
| Zinc lactate | 0.05 |
| Germall plus | 0.2 |
| Ethanol | 70 |
| Incroquat | 0.6 |
| Phenoxyethanol | 0.7 |
| Glycerin | 1.0 |
| Cetyl ethyl (PPG10) | 0.5 |

Rapidity Of Action In Vitro. To test for rapid activity, 0.2 ml of $10^9$ cfu/ml of bacterial culture or $10^6$ cfu/ml of fungal culture (diluted 1:1 with bovine adult serum) was placed in a sterile culture tube and 0.8 ml of the zinc gel was added and mixed. After 15 seconds, the antimicrobial activity was stopped with LTSB (Lecithin-containing Trypticase Soya Broth; a drug-inactivating media) and an aliquot was subcultured on a TSA (Trypticase Soya Agar) plate. The plates were then incubated for 24 hours at 37° C. to determine the number of microbial colonies per tube. Phosphate buffered saline was used instead of gel for the control. As shown in Table 7, no active bacteria or fungi could be recovered from any of the tubes 15 seconds after the addition of zinc gels A, D and G. In contrast, nearly all of the bacteria or fungi could be recovered from the tubes to which PBS was added.

TABLE 7

The Rapid Disinfectant Actions of Hydroalcoholic Gels Containing Zinc Salts

| Organism | Zinc Gel A (cfu/tube) | Zinc Gel D (cfu/tube) | Zinc Gel G (cfu/tube) | Control (cfu/tube) |
|---|---|---|---|---|
| S. aureus | 0 | 0 | 0 | $1.1 \times 10^7$ |
| S. epidermis | 0 | 0 | 0 | $1.0 \times 10^7$ |
| S. aureus (methicillin resistant) | 0 | 0 | 0 | $7.3 \times 10^6$ |
| K. pneumoniae | 0 | 0 | 0 | $3.0 \times 10^7$ |
| E. coli | 0 | 0 | 0 | $2.3 \times 10^6$ |
| C. albicans | 0 | 0 | 0 | $1.5 \times 10^5$ |

Sustainability of Disinfectant Action In Vitro. Hides from freshly killed pigs were obtained from a slaughter house. The skin was washed with water, dehaired and defatted using scalpel. It was then cut into smaller sections, rinsed with water and preserved in sealed plastic bags in a freezer. Before use, a section was removed, thawed and rinsed in water and cut into pieces (3×3 cm) with a blade. These skin pieces were mounted on holders (plastic plates of 5 cm diameter) with epoxy to expose the skin surface. Two pieces of skin were used per sample. 0.3 ml of the test formulation was applied on one piece and rubbed on other piece from a matched pair for 30 sec. After 15 min, one of the two pieces was inoculated with 30 µl of a S. aureus culture ($10^7$ cfu/ml). The two matching skin pieces were rubbed together for 15 sec. After 30 sec, each skin piece was rinsed with LTSB to recover viable organisms and an aliquot from this LTSB wash was subcultured on a D/E plate to quantitate the surviving organisms. Zinc gel without any antiseptic was used as control. As shown in Table 8, Prevacare™ and Avagard™ killed approximately 50% and 90%, respectively, of the bacteria inoculated on the pig skin 15 minutes after their application. In contrast, more than 99.9% of all inoculated bacteria were killed when applied to pig skin 15 minutes after treatment with Zinc gels D or E. These findings indicate that these zinc gels retain their full potency as disinfectants for at least 15 minutes after their use, and therefore are superior to the existing hydroalcoholic gel disinfectants Prevacare™ and Avagard™.

TABLE 8

The Sustainability of the Disinfectant Actions of Hydroalcoholic Gels Containing Zinc Salts

| Formulation | cfu/test |
|---|---|
| Control | $3.0 \times 10^5$ |
| Zinc Gel D | 48 |
| Zinc Gel E | 3 |
| Prevacare ™ | $1.5 \times 10^5$ |
| Avagard ™ | $3.9 \times 10^4$ |

Hydroalcoholic Zinc Gels Fail to Irritate the Skin of Individuals Sensitive to Other Hydroalcoholic Gels. Two volunteers who had previously exhibited sensitivity to the hydroalcoholic gel Prevacare™ were enlisted for this study. Two gm of Prevacare™ or the zinc gel indicated in Table 9 was applied to the palm and spread all over the hands. Skin reactions were observed after 15 minutes of exposure to the gel. The results of these studies are shown in Table 9.

TABLE 9

Hydroalcoholic Zinc Gels Are Not Irritating To individuals
Who Exhibit Sensitivity to Prevacare ™.

| Volunteer | Prevacare ™ | Zinc Gel A | Zinc Gel E |
|---|---|---|---|
| 1 | Redness | None | None |
| 2 | Redness and Itching | None | None |

In an unrelated study of the antimicrobial efficacy of Avagard™, it was also noted that this hydroalcoholic gel also caused skin irritation in some individuals. Thus, the above findings may be of general significance to the prevention of skin irritation induced by alcohol-based disinfectant products.

5.7. Example 7

Evaluation of the Effects of Zinc Salts on the Prevention of Latex-induced Contact Dermatitis Latex gloves are known to cause contact dermatitis in some individuals. Latex-induced contact dermatitis is an especially serious concern among surgeons and other health care workers who face unavoidable exposure to latex in surgical gloves and other medical devices. The following three zinc gel surgical hand preps may be useful in protecting against this problem.

| | (% by wt) |
|---|---|
| ZINC GEL SURGICAL HAND PREP-1 | |
| Water | 33.13 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 60 |
| Incroquat | 0.6 |
| Polawax | 0.5 |
| Zinc stearate | 2.0 |
| Phenoxyethanol | 0.7 |
| Glycerin | 1.0 |
| Cetyl ether (PPG10) | 0.5 |
| Silicone DC1403 | 0.3 |
| ZINC GEL SURGICAL HAND PREP-2 | |
| Water | 30.03 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 63 |
| Incroquat TMS | 0.6 |
| Polawax | 0.3 |
| Stearyl alcohol | 0.3 |
| Zinc stearate | 2.0 |
| Phenoxyethanol | 0.7 |
| Glycerin | 1.0 |
| Cetyl ether (PPG10) | 0.5 |
| Silicone DC1403 | 0.3 |
| ZINC GEL SURGICAL HAND PREP-3 | |
| Water | 29.13 |
| Ucare (JR30) | 0.2 |
| Zinc gluconate | 0.5 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 65 |
| Incroquat | 0.6 |
| Polawax | 0.5 |
| Zinc stearate | 1.0 |
| Phenoxyethanol | 0.7 |
| Glycerin | 1.0 |
| Cetyl ether (PPG10) | 0.5 |
| Silicone DC1403 | 0.3 |

The efficacy of zinc gel surgical hand prep-1 was tested on a volunteer known to develop contact dermatitis when in contact with latex gloves. In this study, the volunteer donned latex gloves and carried out normal activities. After 30 min, redness and irritation was observed on the back or the palm of the hand. Later that same day, after the redness and irritation subsided, the volunteer applied 2 g of the zinc surgical hand prep and, after the alcohol evaporated off, donned latex gloves. No reaction was seen when the gloves were removed after 2 hours. These findings confirm the potential utility of zinc-containing gels to prevent latex-induced contact dermatitis.

5.8. Example 8

The Incorporation of Zinc Salts into Alcohol Gel Wipes Prevents the Irritating Effects of Alcohol While Maintaining Disinfectant Efficacy Individually sealed alcohol-impregnated wipes are useful for the disinfection of topical and various other physical surfaces. When applied topically, however, the alcohol from the wipe may sometimes cause skin irritation. Thus, the addition of zinc salt formulations to alcohol gel wipes is useful in preventing alcohol-induced skin irritation. One such zinc-containing alcohol gel wipe for hand disinfection is composed of the following:

| ZINC GEL X SOLUTION | (% By weight) |
|---|---|
| Water | 20.93 |
| Ucare (JR 30) | 0.2 |
| Zinc gluconate | 0.3 |
| Zinc acetate | 0.1 |
| Zinc lactate | 0.1 |
| Germall plus | 0.2 |
| Chlorhexidine gluconate | 0.05 |
| Benzalkonium chloride | 0.12 |
| Ethanol | 75 |
| Incroquat | 0.6 |
| Polawax | 0.2 |
| Phenoxyethanol | 0.7 |
| Glycerin | 1.0 |
| Cetyl ether (PPG 10) | 0.5 |

Five ml of this solution is dispensed onto each wipe and the wipes are packed in plastic lined bags and sealed for future use as aids in disinfection.

5.9. Example 9

The Incorporation of Zinc Salts into Gels and Creams to Potentiate their Anti-itch Properties Various gels and creams are known in the art for their abilities to treat itchiness or psoriasis. However, some of the ingredients contained in these products may in fact cause irritation in the very individuals they are intended to treat. The incorporation of zinc salt formulations to these products will prevent their irritating properties while retaining their therapeutic effects.

A triple zinc anti-itch aqueous cream or lotion is composed of the following:

| TRIPLE ZINC ANTI-ITCH LOTION | (% by wt) |
| --- | --- |
| Incroquat TMS | 0.8 |
| Polawax NF | 0.8 |
| Petroleum Jelly | 3.0 |
| Crothix | 1.0 |
| Crodomol MM | 1.0 |
| Cremerol | 1.0 |
| Propylene glycol | 2.0 |
| Glycerin | 8.0 |
| Water | 77.3 |
| Ucare JR30 | 0.2 |
| Germall plus | 0.2 |
| Zinc gluconate | 1.0 |
| Zinc acetate | 0.1 |
| Zinc lactate | 0.1 |
| Zinc stearate | 3.0 |
| Zinc oxide | 0.5 |

A triple zinc cream for the treatment of psoriasis is composed of the following:

| TRIPLE ZINC CREAM FOR TREATING PSORIASIS | (% by wt) |
| --- | --- |
| Petroleum Jelly | 25 |
| Incroquat | 1.0 |
| Polawax NF | 1.0 |
| Glycerin | 10.0 |
| Propylene Glycol | 10.0 |
| Crothix | 2.0 |
| Zinc oxide | 3.0 |
| Zinc stearate | 3.0 |
| Allatoin | 0.5 |
| Salicylic acid | 2.0 |
| Dimethicone | 2.0 |
| Water | 38.8 |
| Zinc gluconate | 1.0 |
| Zinc acetate | 0.1 |
| Zinc lactate | 0.1 |
| Germall plus | 0.2 |
| Chlorhexidine gluconate | 0.05 |
| Benzalkonium chloride | 0.05 |
| Ucare JR 30 | 0.2 |

To treat itchiness or psoriasis, a therapeutically effective amount of the triple zinc anti-itch lotion or the triple zinc cream for treating psoriasis is applied to the area to be treated as necessary to maintain the skin surface free or itchiness or the symptoms of psoriasis.

5.10. Example 10

The Incorporation of Zinc Salts into Antimicrobial Gels Containing Chlorhexidine Gluconate and Benzalkonium Chloride does not Reduce Their Antimicrobial Efficacy The antimicrobial agents chlorhexidine gluconate and benzalkonium chloride are known in the art as preservatives in various products. What was not previously appreciated in the art, however, was that the addition of incroquat significantly potentiates the preservative effects of chlorhexidine gluconate and benzalkonium chloride. To demonstrate this synergism between incroquat and chlorhexidine gluconate and benzalkonium chloride, gels with or without chlorhexidine gluconate and benzalkonium chloride or with or without incroquat were examined for the rapidity with which they could kill bacteria in culture. In these studies, 1 ml of $10^8$ cfu of *S. aureus* was mixed with 1.0 ml of Bovine Adult Serum (BAS) and 1.0 ml of the one of the gels indicated below in Table 10. After 15 seconds, a 0.5 ml aliquot was removed and added to 4.5 ml of the drug inactivating media LTSB. The resulting mixture was then diluted 100 fold with LTSB. After mixing, a 0.5 ml aliquot of the diluent was plated on TSA plates, which then were incubated at 37° C. for 24 hours to determine the colony counts.

TABLE 10

Compositions of Gels Containing Various Combinations of Chlorhexidine Gluconate and Benzalkonium Chloride and Incroquat.

| Ingredients | Gel #1 | Gel #2 | Gel #3 | Gel #4 | Gel #5 | Gel #6 |
| --- | --- | --- | --- | --- | --- | --- |
| Water | 33.3 | 33.125 | 33.0 | 32.825 | 32.525 | 32.25 |
| U care (JR30) | 0.2 | 0.2 | 0.2 | 0.2 | 0.2 | 0.2 |
| Ethanol | 65 | 65 | 65 | 65 | 65 | 65 |
| Glycerin | 1.0 | 1.0 | 1.0 | 1.0 | 1.0 | 1.0 |
| Cetylether PPG10) | 0.5 | 0.5 | 0.5 | 0.5 | 0.5 | 0.5 |
| CHG | — | 0.05 | — | 0.05 | 0.05 | 0.05 |
| BZK | — | 0.125 | — | 0.125 | 0.125 | 0.125 |
| Incroquat | — | — | 0.3 | 0.3 | 0.6 | 0.6 |
| Zinc gluconate | — | — | — | — | — | 0.15 |
| Zinc acetate | — | — | — | — | — | 0.1 |
| Zinc lactate | — | — | — | — | — | 0.05 |

As shown in Table 11, the addition of chlorhexidine gluconate and benzalkonium chloride to the gel base (Gel #2) resulted in a ten-fold reduction in the amount of bacteria recovered over that observed with the gel base alone. The addition of incroquat alone to the gel base (Gel #3) only mildly affected the numbers of bacteria that could be recovered at 24 hrs after the addition of the gel to the bacterial culture. However, the addition of chlorhexidine gluconate, benzalkonium chloride and incroquat to the gel base (Gel #4) resulted in a 4-log reduction in the amount of bacteria that could be recovered from the culture. Thus, there is a high degree of synergy between the antibacterial effects of chlorhexidine gluconate and benzalkonium chloride and incroquat.

TABLE 11

The Addition of Incroquat Synergistically Potentiates
the Antimicrobial Effects of Gels Containing Chlorhexidine
Gluconate and Benzalkonium Chloride

| Gel | Bacterial Growth (cfu/tube) | Fold reduction over control |
|---|---|---|
| 1 | $3.0 \times 10^7$ | — |
| 2 | $3.0 \times 10^6$ | 1.0 |
| 3 | $1.6 \times 10^7$ | 0.48 |
| 4 | $3.0 \times 10^3$ | 4.0 |

Having established the strong synergy between chlorhexidine gluconate, benzalkonium chloride and incroquat, it was important to determine whether the further addition of potentially non-irritating zinc salts to this gel would abolish the antimicrobial effects. Thus, the consequences of the addition of zinc salts to gels with chlorhexidine gluconate, benzalkonium chloride and incroquat on their sustained anti-bacterial activity were evaluated using the pig skin model described above in Section 5.6. The results of these studies, shown in Table 12, demonstrate that the addition of zinc (Gel #6) did not interfere with the strong antimicrobial effect seen in gels containing chlorhexidine gluconate, benzalkonium chloride and incroquat (Gel #5) over those seen in gels containing only chlorhexidine gluconate and benzalkonium chloride (Gel #2) or the gel base alone (Gel #1). Thus, zinc salts may be added to antimicrobial gels containing chlorhexidine gluconate, benzalkonium chloride and incroquat to prevent their potential irritation without compromising their antimicrobial effects.

TABLE 12

The Antimicrobial Synergism Observed in Gels Containing
Chlorhexidine Gluconate, Benzalkonium Chloride and Incroquat
is Maintained in the Presence of Zinc Salts

| Gel Formulation | Bacterial Growth (cfu/test) |
|---|---|
| Gel #1 | $1.8 \times 10^5$ |
| Gel #2 | $4.1 \times 10^4$ |
| Gel #5 | $2.0 \times 10^2$ |
| Gel #6 | $1.0 \times 10^2$ |

This finding of synergistic antimicrobial activity between chlorhexidine gluconate, benzalkonium chloride and incroquat in the presence of zinc salts was also observed in alcohol-based gels. For example, as shown in Table 13, a 4-log reduction in bacterial growth was observed in an alcohol-based zinc hydrogel containing chlorhexidine gluconate, benzalkonium chloride and incroquat (gel D; see Section 5.6), as compared to the only 2-log reduction in bacterial growth observed with zinc gel D1 (see Section 5.6), which containing chlorhexidine gluconate and benzalkonium chloride but lacked incroquat. These findings confirm that the addition of incroquat significantly potentiates the preservative effects of chlorhexidine gluconate and benzalkonium chloride, and that these preservative effects are not abolished by the presence of zinc salts within the gel.

TABLE 13

The Addition of Incroquat Potentiates the Antimicrobial
Effects of Zinc Gels Containing Chlorhexidine
Gluconate and Benzalkonium Chloride

| Gel Formulation | Bacterial Growth (cfu/test) |
|---|---|
| Control Base* | $4.0 \times 10^5$ |
| Zinc Gel D1 | $2.0 \times 10^3$ |
| Zinc Gel D | $1 \times 10^2$ |
| Prevacare | $1.5 \times 10^5$ |

*Control base is same as D1 except does not contain Germall plus, chlorhexidine gluconate, benzalkonium chloride and phenoxyethanol.

Synergistic potentiation of antimicrobial activity is also observed in gels containing chlorhexidine gluconate, benzalkonium chloride, incroquat and Sensiva® (octoxyglycerin). Thus, additional studies were performed to establish that the synergistic antimicrobial effects of these compounds was not abolished by the addition of zinc salts to gels containing these ingredients. The compositions of the gels tested are shown in Table 14. The studies were performed using the pig skin model described above in Section 5.6. As shown in Table 15, the addition of zinc (Gel #3) did not interfere with the strong antimicrobial effect seen in gels containing chlorhexidine gluconate, benzalkonium chloride, incroquat and Sensiva® (Gel #2) over those seen in gels containing only Sensiva®& (Gel #5), incroquat (Gel #4), Sensiva® plus incroquat (Gel #6), chlorhexidine gluconate, benzalkonium chloride, and Sensiva® (Gel #1) or the gel base alone (Gel #7). Thus, zinc salts may be added to antimicrobial gels containing chlorhexidine gluconate, benzalkonium chloride, incroquat and Sensiva® to prevent their potential irritation without compromising their antimicrobial effects.

TABLE 14

Compositions of Gels Containing Various Combinations of Chlorhexidine
Gluconate, Benzalkonium Chloride, Incroquat and Sensiva ®.

| Ingredients | Gel #1 | Gel #2 | Gel #3 | Gel #4 | Gel #5 | Gel #6 | Gel #7 |
|---|---|---|---|---|---|---|---|
| Water | 32.125 | 31.525 | 31.225 | 32.7 | 32.3 | 32.9 | 33.3 |
| Ucare | 0.2 | 0.2 | 0.2 | 0.2 | 0.2 | 0.2 | 0.2 |
| Ethanol | 65 | 65 | 65 | 65 | 65 | 65 | 65 |
| Glycerin | 1.0 | 1.0 | 1.0 | 1.0 | 1.0 | 1.0 | 1.0 |
| Cetylether PPG10 | 0.5 | 0.5 | 0.5 | 0.5 | 0.5 | 0.5 | 0.5 |
| CHG | 0.05 | 0.05 | 0.05 | — | — | — | — |
| BZK | 0.125 | 0.125 | 0.125 | — | — | — | — |
| Sensiva ® | 1.0 | 1.0 | 1.0 | — | 1.0 | 1.0 | — |
| Incroquat | — | 0.6 | 0.6 | 0.6 | — | 0.6 | — |
| Zinc gluconate | — | — | 0.15 | — | — | — | — |
| Zinc acetate | — | — | 0.1 | — | — | — | — |
| Zinc lactate | — | — | 0.05 | — | — | — | — |

TABLE 15

The Antimicrobial Synergism Observed in Gels Containing Chlorhexidine Gluconate, Benzalkonium Chloride, Incroquat and Sensiva ® is Maintained in the Presence of Zinc Salts

| Gel Formulation | Bacterial Growth (cfu/test) |
| --- | --- |
| Gel #1 | $7.9 \times 10^2$ |
| Gel #2 | $3.0 \times 10^1$ |
| Gel #3 | $2.0 \times 10^1$ |
| Gel #4 | $1.6 \times 10^5$ |
| Gel #5 | $2.9 \times 10^4$ |
| Gel #6 | $3.0 \times 10^3$ |
| Gel #7 | $3.0 \times 10^5$ |

5.11. Example 11

The Incorporation of Zinc Salts into Hydroalcoholic Gels Containing 1.0% Chlorhexidine Prevents the Irritating Effects of Alcohol and Chlorhexidine While Maintaining Disinfectant Efficacy Latex gloves are beneficial in minimizing or preventing transmission of various infectious agents, but an increasing proportion of the population is developing an allergic reaction to latex that results in the development of contact dermatitis. Because zinc salts can prevent the irritation caused by latex, the addition of zinc salts to hydroalcoholic gels or creams to be applied to the skin underneath the glove will be useful in preventing this latex-induced contact dermatitis. Furthermore, if the hydroalcoholic gels also comprise 1.0% chlorhexidine, the barrier to the transmission of infectious agents will be further improved provided that the zinc salts do not inactivate the antimicrobial effects of the chlorhexidine. The following formulation therefore will be useful as a topical disinfectant to be applied to skin subsequently covered by latex articles.

| HYDROALCOHOLIC ZINC GEL CONTAINING 1.0% CHLORHEXIDINE FOR LONG TERM ACTIVITY | (% by wt) |
| --- | --- |
| Water | 25.25 |
| Ucare (JR 30) | 0.15 |
| Hydroxypropylmethylcellulose (K-100) | 0.15 |
| Germall plus | 0.2 |
| Zinc gluconate | 1.0 |
| Zinc acetate | 0.2 |
| Zinc lactate | 0.1 |
| Chlorhexidine gluconate (20%) | 5.0 |
| Benzalkonium chloride (50%) | 0.25 |
| Ethanol | 60 |
| Incroquat | 0.7 |
| Polawax | 0.3 |
| Phenoxyethanol | 0.7 |
| Glycerin | 2.0 |
| Cetylether (PPG 10) | 1.0 |
| Vitamin E | 0.2 |
| Zinc stearate | 3.0 |

The efficacy of the gel described immediately above was tested on a volunteer known to develop contact dermatitis when in contact with latex gloves. In this study, the volunteer applied 2 g of the hydroalcoholic zinc gel containing 1.0% chlorhexidine and, after the alcohol evaporated off, donned latex gloves and carried out normal activities. No reaction was seen when the gloves were removed after 3 hours. These findings confirm the potential utility of zinc-containing gels to prevent latex-induced contact dermatitis.

5.12. Example 12

Topical Creams Containing Triple Zinc Salts Protect Against Dermal Irritation Caused by Various Physical, Chemical, Mechanical or Biological Irritants A topical triple zinc anti-itch cream or lotion of the following composition was prepared:

| TRIPLE ZINC ANTI-ITCH LOTION | (% by wt) |
| --- | --- |
| Incroquat TMS Behenyl | 0.8 |
| Polawax NF | 0.8 |
| Petroleum Jelly | 3.0 |
| Crothix | 1.0 |
| Crodomol MM | 1.0 |
| Cremerol HMG | 1.0 |
| Propylene glycol | 2.0 |
| Glycerin | 8.0 |
| Water | 77.3 |
| UCare JR30-M | 0.2 |
| Germall plus | 0.2 |
| Zinc gluconate | 0.3 |
| Zinc acetate | 0.1 |
| Zinc lactate | 0.1 |
| Zinc stearate | 3.0 |
| Zinc oxide | 0.5 |

The topical triple zinc anti-itch lotion then was tested on volunteers to determine whether it could protect against the skin irritation resulting from dryness (e.g. winter itch), prickly heat, mechanical insult (e.g. shaving or abrasive procedures), contact with poison ivy, diaper rash, contact with detergents such as sodium lauryl sulfate, nonoxinol-9, chemical agents, antimicrobial agents, alcohol, etc. The results of these studies are described in Table 16.

TABLE 16

Evaluation of Topical Triple Zinc Anti-itch Lotion in Prevention of Skin Irritation Caused by Physical, Chemical, Mechanical or Biological Irritants

| Problem/Irritant | Number of volunteers tested | Time after application required for cessation of irritation/wound healing |
| --- | --- | --- |
| Winter itch* | 4 | 10–15 minutes |
| Prickly heat | 1 | 15–20 minutes |
| Skin irritation after shaving | 2 | 5–10 minutes |
| Poison ivy | 2 | 10–15 minutes |
| psoriasis itch | 2 | 10–20 minutes |
| scratch wound | 1 | 2 days |

*Two of the four volunteers tried the same lotion without zinc gluconate, zinc acetate and zinc lactate, but the irritation ceased only after several applications.

Based on these observations, this triple zinc anti-itch lotion reduces the skin irritation produced by a wide range of irritants, including those of physical, chemical, biological, or mechanical origins.

5.13. Example 13

Topical Creams Containing Triple Zinc Salts Protect Against Dermal Irritation Caused by Essential Oils (EO) and Fragrance and Flavor (FF) Chemicals

Essential oils are volatile oils obtained from plant or animal sources and are composed of complex mixtures of several constituents as monoterpenes and sesquiterpene hydrocarbons, monoterpene and sesquiterpene alcohols, esters, ethers, aldehydes, ketones, oxides and the like. These essential oils and their isolated constituents have been mainly used as fragrance and flavor agents in several formulations. These essential oils have also been known to show antimicrobial, anti-inflammatory and wound-healing properties.

However, there have been several reports about the skin-sensitizing effect of these essential oils. The spectrum of reported skin reactions to essential oils includes contact dermatitis, irritant contact dermatitis, phototoxic reactions and urticaria. See De Groot A, Frosch P J. Adverse reactions to fragrances: a clinical review. *Contact Dermatitis* 1997;36:57-86. A mixture of almond, ylang-ylang, neroli, sandalwood and frankincense oils was shown to have resulted in a positive patch-test on a patient whose skin was exposed to the mixture of these oils. See Bleasel N, Tate B and Rademaker M. Allergic contact dermatitis following exposure to essential oils. *Australian Journal of Dermatology* 2002;43:211-213. Repeated intradermal dosing with peppermint oil was reported to have produced moderate and severe reactions in rabbits. See Nair B. Final report on the safety assessment of Mentha Piperita (Peppermint) oil, Mentha Piperita (Peppermint) Leaf extract, Mentha Piperita (Peppermint) leaf and Mentha Piperita (Peppermint) water. *International Journal of Toxicology* 2001 ;20(Suppl 3):61-73.

Researchers have also shown that lavender oil is responsible for contact dermatitis using the patch testing method, which was carried out for a period of 9 years. See Sugiura M, Hayakawa R, Kato Y, Sugiura K, Hashimoto R. Results of patch testing with lavender oils in Japan, *Contact Dermatitis* 2000;43:157-160. Jasmine absolute, geranium oil bourbon, spearmint oil, clove oil, lemongrass oil and cedarwood oil also have been shown to produce allergic contact dermatitis. See generally Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). *Contact Dermatitis* 2001;44:344-346; and Wohrl S, Hemmer W, Focke M, Gotz M, Jarisch R. The significance of fragrance mix, balsam of Peru, colophony and propolis as screening tools in the detection of fragrance allergy. *British Journal of Dermatology* 2001;145(2):268-273. There has been a recent report that a girl who was using a fragrance containing the essential oil of tangerine, suffered from itching erythema and papules on areas of contact on the hands, face and neck. See Vilaplana J, Romaguera C. Contact dermatitis from the essential oil of tangerine in fragrances. *Contact Dermatitis* 2002;46:108.

Apart from the essential oils, their individual ingredients, either isolated from the oil or chemically synthesized have also been show to have skin sensitizing effect. L-citronellol, α-amylcinnamaldehyde and lyral have been shown to test positive to skin sensitization tests. See Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). *Contact Dermatitis* 2001 ;44: 344-346. Geraniol, farnesol, hydroxycitronellal, isoeugenol, and eugenol have also been reported to test positive to skin patch-tests See Larsen W, Nakayama H, Fischer T, Elsner P, Frosch P, Burrows D, Jordan W, Shaw S, Wilkinson J, Marks J Jr, Sugawara M, Nethercott M, Nethercott J. Fragrance contact dermatitis: a worldwide multicenter investigation (Part II). *Contact Dermatitis* 2001;44:344-346 and Wohrl S, Hemmer W, Focke M, Gotz M, Jarisch R. The significance of fragrance mix, balsam of Peru, colophony and propolis as screening tools in the detection of fragrance allergy. *British Journal of Dermatology* 2001;145(2):268-273. Eucalyptol was shown to result in the appearance of pruritus and erythema on the skin of an athlete, who was using a cream containing eucalyptol. See Vilaplana J, Romaguera C. Contact dermatitis from the essential oil of tangerine in fragrances. *Contact Dermatitis* 2002;46:108.

In order to incorporate essential oils, their isolated ingredients and other natural or synthetic fragrance and flavor chemicals in topical formulations without causing contact dermatitis, the following topical formulations containing the triple zinc salts with and without essential oils (EO) and fragrance and flavor chemicals (FF) were prepared in aqueous and alcohol base:

Alcohol Zinc Fel Hand Wash #1

| Ingredient | % by weight |
| --- | --- |
| UCare JR30-M | 0.05 |
| Methocel K100 | 0.1 |
| Water | 36.08 |
| Zinc gluconate | 0.3 |
| Zinc acetate | 0.1 |
| Zinc lactate | 0.1 |
| Germall Plus | 0.2 |
| Ethanol | 58 |
| Ispropanol | 2.0 |
| Silicone (Dimethicone) | 0.2 |
| Incroquat Behentyl TMS | 0.7 |
| Polawax A31 | 0.3 |
| Glycerin | 1.0 |
| Cetyl ether (PPG10) | 0.5 |
| CHG | 0.05 |
| BZK | 0.02 |
| Farnesol | 0.3 |

Alcohol Zinc Gel for use Under Latex Glove

| Ingredients | % by weight |
| --- | --- |
| Ucare JR30-M | 0.8 |
| Methocel K100 | 0.3 |
| Water | 27.13 |
| Zinc gluconate | 0.6 |
| Zinc acetate | 0.2 |
| Zinc lactate | 0.2 |
| Germall Plus | 0.2 |
| Zinc stearate | 1.5 |
| Zinc oxide | 1.0 |
| Glucate DO | 5.0 |
| Ethanol | 55.0 |
| Ispropanol | 3.0 |
| Silicone (Dimethicone) | 0.5 |
| Incroquat Behenyl TMS | 1.0 |
| Polawax A31 | 0.5 |
| Glycerin | 2.0 |

-continued

| Ingredients | % by weight |
| --- | --- |
| Cetyl ether (PPG10) | 1.0 |
| CHG | 0.05 |
| BZK | 0.02 |
| Farnesol | 0.3 |
| Vitamin E | 0.2 |

Triple Zinc Anti-itch Lotion with EO and FF Ingredients

| Ingredients | (% by wt) |
| --- | --- |
| Incroquat Behenyl TMS | 0.8 |
| Polawax NF | 0.8 |
| Petroleum Jelly | 3.0 |
| Crothix | 1.0 |
| Crodomol MM | 1.0 |
| Cremerol | 1.0 |
| Propylene glycol | 2.0 |
| Glycerin | 8.0 |
| Water | 77.4 |
| Ucare JR30 | 0.2 |
| Germall + | 0.2 |
| Zinc gluconate | 0.3 |
| Zinc acetate | 0.1 |
| Zinc lactate | 0.1 |
| Zinc stearate | 3.0 |
| Zinc oxide | 0.5 |
| Farnesol | 0.3 |
| Lemon oil | 0.3 |

Anti-irritant Disinfectant Soap with EO AND FF Ingredients

| Ingredients | % By weight |
| --- | --- |
| Polyox WSR 205 | 0.1 |
| UCare Jr30-M | 0.2 |
| Germall Plus | 0.2 |
| Water | 86.93 |
| Pluronic F87 | 2.0 |
| Cocoamidopropylbetaine | 1.0 |
| Mirapol A-15 | 1.0 |
| Propylene glycol | 2.0 |
| Polyquaternium-47(Merquat 3330) | 3.0 |
| Glycerin | 2.0 |
| CHG | 0.05 |
| BZK | 0.12 |
| Triclosan | 0.3 |
| Farnesol | 0.3 |
| Lemon oil | 0.3 |
| Zinc acetate | 0.1 |
| Zinc lactate | 0.1 |
| Zinc gluconate | 0.3 |

5.14. Example 14

Anti-irritant Antimicrobial Compositions Containing Zinc Salts and Panthenol Protect Against Dermal Irritation Although anti-irritant compositions containing two or more soluble zinc salts such as those described above can reduce skin irritation, hydroalcoholic formulations containing zinc salts at concentrations above 0.5% may be unstable, due either to interaction between zinc salts with other ingredients or to insolubility of the zinc salts in the alcohol. However, when lower concentration of zinc salts are used (0.1%-0.5%), the stability of the formula may be improved at the expense of its anti-irritant properties.

D,L panthenol is used as a deep penetrating moisturizer and is reported to have wound healing and anti-inflammatory effects when used in topical formulations. The effects of the addition of panthenol to antimicrobial/anti-irritant compositions containing zinc salts were evaluated. In these studies, the following compositions were generated and analyzed for their ability to reduce or prevent the potentially irritating effects of antiperspirants or aftershave lotions:

| Stock solutions: | |
| --- | --- |
| Ingredients | % (wt/wt) |
| (1) Gel with panthenol | |
| Water | 88.0 |
| U-care JR 30M | 2.0 |
| D,L Panthenol 50W (50% in water) | 10.0 |
| (2) Gel with soluble zinc salts | |
| Water | 95.0 |
| U-care JR 30M | 2.0 |
| Zinc acetate | 1.0 |
| Zinc gluconate | 1.0 |
| Zinc lactate | 1.0 |
| (3) Gel with only zinc salts + panthenol | |
| water | 85.0 |
| U-care JR 30M | 2.0 |
| Zinc Acetate | 1.0 |
| Zinc lactate | 1.0 |
| Zinc gluconate | 1.0 |
| D,L Panthenol 50W | 10.0 |
| (4) Gel with soluble and insoluble organic zinc salts | |
| Water | 90.0 |
| U-care JR 30M | 2.0 |
| Zinc acetate | 1.0 |
| Zinc gluconate | 1.0 |
| Zinc lactate | 1.0 |
| Zinc stearate | 5.0 |
| (5) Gel with soluble and insoluble organic zinc salts + panthenol | |
| Water | 80.0 |
| U-care JR 30M | 2.0 |
| Zinc Acetate | 1.0 |
| Zinc lactate | 1.0 |
| Zinc gluconate | 1.0 |
| Zinc stearate | 5.0 |
| D,L Panthenol 50W | 10.0 |

(1) A gel with only panthenol
(2) A gel with only soluble zinc salts
(3) A gel with soluble zinc salts + panthenol
(4) A gel with soluble zinc salts + insoluble zinc salts
(5) A gel with soluble zinc salts + insoluble zinc salts + panthenol A volunteer who is sensitive to antiperspirant and alcohol-containing aftershave lotion was selected for the test. 10% of each of the gels was incorporated into 90% of the antiperspirant. After showering, the volunteer applied 1 g. of the gel on the under arm area of one side of the body and the control antiperspirant to the under arm area on the other side of the body. The reaction then was noted. This experiment was repeated with the other four gels on the next four consecutive days.

The results were quantified as follows. A severe response was given a score of '3+,' a moderate response a score of '2+,' a mild response a score of '1+,' and no response a score of '0.' The results of the study are presented in Table 17.

TABLE 17

Gels containing zinc salts and panthenol prevented the stinging and itching associated with antiperspirants

|  | Stinging | Itching |
|---|---|---|
| Control | 1+ | 2+ |
| Gel 1 | 0 | 2+ |
| Gel 2 | 0 | 1+ |
| Gel 3 | 0 | 0.5+ |
| Gel 4 | 0 | 1+ |
| Gel 5 | 0 | 0 |

A similar study was performed using an alcohol-containing aftershave lotion. The lotion was prepared as follows:

| Ingredients | % (wt/wt) |
|---|---|
| Ethanol | 40.0 |
| Water | 58.8 |
| U-care JR 30M | 0.2 |
| Glycerin | 1.0 |

Gels 1, 2 and 3, which did not contain zinc stearate, then were mixed with an alcohol-containing aftershave lotion, at a ratio of 10% gel:90% aftershave, and tested in the volunteer, who applied 0.5 g of the control lotion to one side of the face and the same amount of the test lotion to the other side of the face immediately after shaving. The other two lotions were tested similarly on each of the next two consecutive days.

The results of these studies are shown in Table 18. Scoring of the response was performed as described immediately above for the antiperspirant studies.

TABLE 18

Lotions containing zinc salts and panthenol prevented the stinging and irritation associated with alcohol-based aftershave lotion

|  | Scoring | |
|---|---|---|
|  | Stinging | Erythema |
| Control Lotion | 2+ | 1+ |
| Lotion with Gel 1 (Panthenol) | 2+ | 1+ |
| Lotion with Gel 2 (Zinc salts) | 1+ | 0.5+ |
| Lotion with Gel 3 (Zinc salts + Panthenol) | 0 | 0 |

Anti-irritant compositions containing two or three soluble organic zinc salts (0.1-0.5%), D,L Panthenol (0.5-2%) and a cellulose polymer gelling agent (0.1-0.5%) also were prepared. The cellulose polymers studied were polyquaternium-10 and hydroxy propyl methyl cellulose. The compositions were as follows:

| Ingredients | %(wt/wt) |
|---|---|
| Zinc Gel A | |
| Water | 85.0 |
| U-care JR30M | 2.0 |
| Zinc acetate | 1.0 |
| Zinc lactate | 1.0 |
| Zinc gluconate | 1.0 |
| D,L Panthenol 50W | 10.0 |
| Zinc Gel B | |
| Water | 84.0 |
| U-care JR30M | 2.0 |
| Zinc lactate | 2.0 |
| Zinc gluconate | 2.0 |
| D,L Panthenol 50W | 10.0 |
| Zinc Gel C | |
| Water | 83.0 |
| U-care JR 30M | 2.0 |
| Hydroxypropyl methyl cellulose (Methocell K4MS) | 1.0 |
| Zinc lactate | 2.0 |
| Zinc gluconate | 2.0 |
| D,L Panthenol 50W | 10.0 |
| Zinc Gel D | |
| Water | 79.0 |
| U-care JR30 | 2.0 |
| Zinc lactate | 2.0 |
| Zinc gluconate | 2.0 |
| Zinc stearate | 5.0 |
| D,L Panthenol 50W | 10.0 |

These zinc gels also can be incorporated into antiperspirants, aftershave lotions, hydroalcoholic skin disinfectants, therapeutic creams etc.

Anti-irritant zinc compositions containing two soluble organic zinc salts and panthenol were prepared in an aqueous base, and their effects on preventing skin irritation induced by alcohol was evaluated in a volunteer. In these studies, the anti-irritant composition was prepared in a clear formulation composition containing only soluble zinc salts and panthenol. An anti-irritant zinc/panthenol composition ("zinc panthenol 1") was prepared with the following composition:

| Zinc gluconate | 2.0% |
|---|---|
| Zinc lactate | 2.0% |
| Panthenol 50W | 10.0% |
| Water | 86.0% |

Using this zinc/panthenol solution, the following alcohol splash formulations were prepared for testing:

| Ingredients | % |
|---|---|
| Formulation A | |
| Zinc Panthenol 1 | 10 |
| Alcohol SD 40 | 30 |
| Glycerin | 1.0 |
| Glucam P 20 | 1.0 |
| Water | 58 |
| Formulation B | |
| Alcohol SD 40 | 30 |
| Glycerin | 1.0 |
| Glucam P 20 | 1.0 |
| Panthenol 50W | 10.0 |
| Water | 68.0 |
| Formulation C | |
| Zinc gluconate | 0.2 |
| Zinc lactate | 0.2 |
| Alcohol SD 40 | 30 |

-continued

| Ingredients | % |
|---|---|
| Glycerin | 1.0 |
| Glucam P 20 | 1.0 |
| Water | 67.6 |

Formulations A, B and C were tested in a volunteer, who applied 0.5 g of the control splash to one side of the face and the same amount of the test splash to the other side of the face immediately after shaving. The other two splashes were tested similarly on each of the next two consecutive days.

The results of these studies are shown in Table 19. Scoring of the response was performed as described immediately above for the antiperspirant and aftershave studies reported in Tables 17 and 18, respectively.

TABLE 19

Aqueous formulations containing zinc salts and panthenol prevented the stinging and irritation associated with alcohol-based aftershave lotions.

|  | Irritation | Stinging |
|---|---|---|
| Splash A | 0 | 0 |
| Splash B | 1+ | 1+ |
| Splash C | 0.5+ | 1+ |

The following zinc/panthenol anti-irritant compositions also were prepared:

(1) Alcohol-based Anti-irritant Cream for use Under Latex Glove

| Ingredients | Percent |
|---|---|
| Water | 23.57 |
| Zinc acetate | 0.1 |
| Zinc lactate | 0.1 |
| Zinc gluconate | 0.3 |
| Methocell K4MS | 0.3 |
| UcareJR 30 | 0.3 |
| Glycerin | 1.0 |
| Panthenol 50W | 1.0 |
| Alcohol.SDA-3C | 67.6 |
| Cromollient DP3A | 2.0 |
| Incroquat BA 85 | 0.5 |
| Phenoxy ethanol | 0.7 |
| Incroquat TMS Behenyl | 0.7 |
| Polowax A-31 | 0.3 |
| PHMB | 0.15 |

(2) Alcohol-based Anti-irritant Surgical Prep

| Ingredients | Percent |
|---|---|
| Water | 22.27 |
| Zinc lactate | 0.2 |
| Zinc gluconate | 0.2 |
| Methocell K4MS | 0.1 |
| UcareJR 30 | 0.2 |
| Panthenol 50W | 1.0 |
| Alcohol.SDA-40B | 72.7 |
| CrodamolSTS | 1.0 |
| Incroquat BA 85 | 0.3 |
| Procetyl 10 | 0.5 |
| PHMB | 0.15 |
| Farnesol | 0.3 |
| BZT | 0.18 |
| Propylene Glycol | 1.0 |

(3) Health Care Hand Disinfectant

| Ingredients | Percent |
|---|---|
| Water | 22.27 |
| Zinc lactate | 0.2 |
| Zinc gluconate | 0.2 |
| Methocell K4MS | 0.1 |
| UcareJR 30 | 0.2 |
| Panthenol 50W | 1.0 |
| Alcohol.SDA-40B | 72.7 |
| CrodamolSTS | 1.0 |
| Incroquat BA 85 | 0.3 |
| Procetyl 10 | 0.5 |
| PHMB | 0.15 |
| Farnesol | 0.3 |
| BZT | 0.18 |
| Propylene Glycol | 1.0 |

(4) Anti-irritant Skin Lotion

| Ingredients | Percent |
|---|---|
| Water | 83.75 |
| Zinc lactate | 0.1 |
| Zinc gluconate | 0.3 |
| Zinc acetate | 0.1 |
| Polyox WSR 205 | 0.1 |
| Kytamer | 0.15 |
| UcareJR 30 | 0.1 |
| Panthenol 50W | 1.0 |
| Germal+ | 0.2 |
| Petroleum Jelly | 1.0 |
| Crodamol GTCC | 2.0 |
| Incroquat TMS Behenyl | 3.5 |
| Polowax NF | 3.0 |
| Gycerin | 2.0 |
| Crodacol S95 | 1.0 |
| Zinc stearate | 0.5 |
| Zinc oxide | 0.5 |
| Farnesol | 0.3 |
| Lemon oil | 0.3 |

The present invention further provides for an anti irritant zinc composition for application on the surface of latex gloves. To reduce latex glove-related contact dermatitis, gloves can be coated with the following anti irritant zinc slurry:

| Ingredients | % wt/wt |
|---|---|
| Zinc gluconate | 1–.5 |
| Zinc lactate | 1–.5 |
| D,L Panthenol (50 W) | 5–40 |
| Glycerine | 20–50 |
| Zinc oxide | 2–10 |
| Zinc stearate | 2–10 |

10-20% of this Zinc slurry can be incorporated into the Silicone or polyurethane fluid used as lubricant on the surface of the glove

5.15. Example 15

Antimicrobial Compositions Containing Synergistic Combinations of Emollient Solvents and Essential Oils and/or Constituents Thereof and/or Anti-inflammatory Agents Antimicrobial agents such as biguanides, quaternary ammonium compounds and the like are presently used as preservative/antimicrobial agents in skin-care formulations. However, these agents are potentially irritating to certain individuals. Some of these antimicrobial agents can also cause resistance in microorganisms when used over an extended period of time.

Emollient solvents (ES) such as octoxyglycerine (Sensiva®), pentylene glycol (Hydrolite-5), 1,2-hexanediol and caprylyl glycol (the synergistic mixture called Symdiol-68) have been known to exhibit antimicrobial activity, especially against gram-positive organisms and these have been used in combination with certain deodorizing actives to obtain efficient deodorizing compositions. See U.S. Pat. No. 5,516,510. These compounds also provide excellent emolliency when used in topical formulations. Previous studies have shown that emollient solvents such as Sensiva® produce a synergistic antimicrobial effect when used in combination with other previously-known antimicrobial agents. See U.S. patent Publication US2003/0152644.

Essential oils are volatile oils obtained from plant or animal sources and are composed of complex mixtures of several active agents, such as monoterpene and sesquiterpene hydrocarbons, monoterpene and sesquiterpene alcohols, esters, ethers, aldehydes, ketones, oxides, and the like. These essential oils (EO) and their active agents (or individual constituents, "ICs"), either isolated from essential oils or chemically synthesized, have been mainly used as fragrance and flavor agents in several formulations. These EOs and ICs have also been known to show antimicrobial, anti-inflammatory and wound-healing properties.

In order to develop a disinfectant composition that does not contain antimicrobials, the efficacy of various combinations of ES and EO/IC was evaluated to determine whether they would exhibit synergistic activity and broad spectrum antimicrobial activity. The effects of the addition of anti-inflammatory agents (AI) such as salicylic acid and their derivatives-zinc salicylate and acetyl salicylic acid (aspirin) on the antimicrobial effects of the disinfectant composition were also evaluated.

In these studies, an alcoholic gel base was prepared and these ES and the EOs and/or ICs and/or AIs were incorporated. The rapid antimicrobial activity of these preparations was then assessed to determine whether they exhibited synergistic antimicrobial activity. Surprisingly, it was discovered that ES and EO/IC exhibit synergistic rapid antimicrobial activity against both-gram positive and gram-negative bacteria. Similarly, the ES and EO/IC also exhibit synergistic rapid antimicrobial activity with AIs. Alcohol-based gels containing synergistic combinations of the ES and IC and/or AI were then formulated and their antimicrobial activity was evaluated and compared with the gels containing antimicrobials in the pig skin model (PSM). In addition, various topical alcohol-based antimicrobial formulations containing ES and EOs and/or ICs and/or AIs were developed.

In these studies, an alcohol-based gel was prepared as follows:

| Alcohol Gel Base - 1 | |
|---|---|
| Ingredient | % by weight |
| UCare JR 400 | 0.1 |
| Method K100M | 0.1 |
| Water | 40.0 |
| Germall Plus | 0.3 |
| Ethanol | 55.0 |
| Ispropanol | 2.0 |
| Incroquat Bethenyl TMS | 0.7 |
| Polawax A31 | 0.3 |
| Glycerin | 1.0 |
| PPG-10 Cetyl ether (Procetyl-10) | 0.5 |

The ES, EOs and/or ICs and/or AIs were incorporated in the Gel Base-1 and the rapid antimicrobial activity of the resultant gel was evaluated against *S. aureus* and *E. coli*. To determine the efficacy of the antimicrobial composition on the skin, which may be contaminated with blood or other proteinaceous fluids containing bacteria, the rapid activity was evaluated in presence of serum using the following method.

0.5 ml of $10^8$ CFU/ml of *S. aureus* (or *E. coli*) was added to 0.5 ml of bovine adult serum in a sterile culture tube and mixed. 0.5 ml of the formulation was added to the tube and vortexed for 15 seconds. This mixture then was further diluted 1:100 with drug inactivating media (LTSB) and 0.5 ml of the diluted mixture was plated on a TSA plate. The plates were incubated at 37° C. for 24 hours and the colony count per ml of culture was determined. The Gel Base-1 was taken as the control. The results of these studies are shown in Tables 20-23.

Table 20: Synergistic Activity of EOs or ICs against *E. coli* in Alcohol-based Gels Test organism: *E. coli*

TABLE 20

Synergistic activity of EOs or ICs against *E. coli* in alcohol-based gels
Test organism: *E. coli*

| Groups | cfu/ml | $\log_{10}$ reduction |
|---|---|---|
| Gel Base (Control) | $6.2 \times 10^7$ | — |
| F (0.5) | $1.0 \times 10^6$ | 1.8 |
| LO (0.5) | $2.6 \times 10^6$ | 1.3 |
| PXE (0.5) | $1.6 \times 10^6$ | 1.5 |
| SEN (0.25) | $8.0 \times 10^5$ | 1.9 |
| SYM (1.0) | $4.6 \times 10^6$ | 1.1 |
| SEN (0.25) + LO (0.5) | $2.0 \times 10^2$: | 5.5 |
| SEN (0.25) + F (0.5) | $4.0 \times 10^3$ | 4.2 |
| SEN (0.25) + PXE (0.5) | $1.9 \times 10^3$ | 4.5 |
| SYM (1.0) + F (0.5) | $3.2 \times 10^3$ | 4.3 |
| SEN (0.25) + F (0.5) + SYM (1.0) | $1.3 \times 10^2$ | 5.7 |
| SEN (0.25) + F (0.5) + PXE (0.5) | $1.9 \times 10^3$ | 4.5 |

Notes: Figures in brackets are the concentration of the ingredients (% w/w) that were added to Alcohol Gel Base-1.
F: Farnesol;
LO: Lavender oil;
PXE: Phenoxyethanol;
SEN: Sensiva ®; and
SYM: Symdiol-68.

The results shown in Table 20 demonstrate that Sensiva® (an ES) acts synergistically with an EO (lavender oil) to produce a 5.5-$\log_{10}$ reduction in colony formation. Sensiva® also acts synergistically with an IC (farnesol, an active agent of the essential oils derived from lemongrass, tuberose and petitgrain), to produce a 4.2-$\log_{10}$ reduction in colony formation. Furthermore, Sensiva® acts synergistically with phenoxyethanol, a constituent of sage oil, to produce a 4.5-$\log_{10}$ reduction in colony formation. Similarly, symdiol (an ES) and farnesol (an IC) show good synergistic action against *E. Coli* (a 4.3-$\log_{10}$ reduction in colony formation).

The antimicrobial activity of the Sensiva®-farnesol combination can be further enhanced if symdiol (an ES) is added along with these ingredients (a 5.7-$\log_{10}$ reduction). Hence, a synergistic combination of ES and EO or ICs can be used to obtain rapid antimicrobial activity against gram-negative microorganisms as *E. coli*.

TABLE 21

Synergistic activity of ES and EOs or ICs against *S. aureus* in alcohol-based gels
Test organism: *S. aureus*

| Groups | cfu/ml | $\log_{10}$ reduction |
| --- | --- | --- |
| Gel Base (Control) | $5.0 \times 10^7$ | — |
| F (0.5) | $3.3 \times 10^6$ | 1.2 |
| F (1.0) | $3.3 \times 10^6$ | 1.2 |
| PXE (0.5) | $7.9 \times 10^5$ | 1.8 |
| LO (1.0) | $3.5 \times 10^6$ | 1.1 |
| SYM (1.0) | $3.2 \times 10^6$ | 1.2 |
| SEN (1.0) | $2.5 \times 10^6$ | 1.3 |
| SEN (2.0) | $1.6 \times 10^4$ | 3.5 |
| LO (1.0) + SEN (1.0) | $2.3 \times 10^4$ | 3.3 |
| LO (1.0) + SYM (1.0) | $2.4 \times 10^6$ | 1.3 |
| F (1.0) + SEN (1.0) | $9.1 \times 10^4$ | 2.7 |
| PXE (0.5) + SEN (2.0) | $1.2 \times 10^4$ | 3.6 |
| F (0.5) + SEN (2.0) | $2.4 \times 10^4$ | 3.6 |
| LO (1.0) + SEN (1.0) + SYM (1.0) | $2.6 \times 10^3$ | 4.3 |
| PXE (0.5) + SEN (2.0) + F (0.5) | $3.2 \times 10^3$ | 4.2 |

Notes:
Figures in brackets are the concentration of the ingredients (% w/w) that were added to Alcohol Gel Base-1.
F: Farnesol;
LO: Lavender oil;
PXE: Phenoxyethanol;
SEN: Sensiva ®; and
SYM: Symdiol-68.

The results shown in Table 21 demonstrate that the combination of lavender oil (an EO) and Sensiva® (an ES) show synergistic rapid antimicrobial action against *S. aureus* (a 3.3-$\log_{10}$ reduction in growth). Symdiol-68 (another ES) does not show synergism with lavender oil, but does potentiate the synergistic activity of the lavender oil-Sensiva(V combination (a 4.3-$\log_{10}$ reduction). Sensiva® also shows synergy with farnesol (an IC) in its antimicrobial action against *S. aureus*, but to a somewhat lesser degree (a 2.7-$\log_{10}$ reduction). Sensiva® did not show any synergistic activity with PXE against this organism. Thus, an ES (Sensiva®) acts synergistically with an EO (lavender oil) in its antimicrobial action against the gram-positive *S. aureus*, and addition of another ES (Symdiol-68) further enhances the activity of the synergistic combination.

Lavender oil has a strong fragrance and therefore its use may not be desirable in certain formulations. Since farnesol also shows synergistic activity with Sensiva®, the antimicrobial activity of the combination of Sensiva®, farnesol and PXE was determined against *S. aureus*, and was found to be comparable (a 4.2-$\log_{10}$ reduction in bacterial growth to the combination of Sensiva®®, lavender oil and Symdiol. The combination of Sensiva®, farnesol and PXE therefore can be used to give comparable antimicrobial activity against *S. aureus* as the combination of Sensiva®, lavender oil, and symdiol in formulations where the odor of lavender oil is undesirable.

TABLE 22

Synergistic activity of AIs (aspirin or zinc salicylate) with ES against *E. coli* in alcohol-based gels
Test organism: *S. aureus*

| Groups | cfu/ml | $\log_{10}$ reduction |
| --- | --- | --- |
| Gel Base (Control) | $4.9 \times 10^7$ | — |
| ASP (2) | $7 \times 3\ 10^5$ | 1.8 |
| SEN (0.2) | $9.0 \times 10^5$ | 1.8 |
| PXE (0.5) | $1.6 \times 10^6$ | 1.5 |
| SEN (0.2) + ASP (2) | $2.3 \times 10^3$ | 4.3 |
| SEN (0.2) + ZS (2) | $6.7 \times 10^1$ | 5.8 |
| SEN (0.5) + ASP (2) + PXE (0.5) | $6.7 \times 10^1$ | 5.8 |
| SEN (0.2) + ZS (2) + PXE (0.5) | $6.7 \times 10^1$ | 5.8 |

Notes:
Figures in brackets are the concentration of the ingredients (% w/w) that were added to Alcohol Gel Base-1.
ASP: Acetyl salicylic acid (aspirin);
PXE: phenoxyethanol;
SEN: Sensiva ®;
ZS: zinc salicylate.

The results presented in Table 22 demonstrate that the AIs aspirin and zinc salicylate show synergism with Sensiva® (an ES) in its antimicrobial activity against *E. coli*. The addition of PXE (an IC) further potentiates the antimicrobial activity. Salicylic acid also shows synergy with both Sensiva® (an ES) and PXE (and ES) in its antimicrobial activity against *S. aureus* (Table 23).

TABLE 23

Synergistic activity of AI (salicylic acid) with ES and IC against *S. aureus* in alcohol-based gels
Test organism: *S. aureus*

| Groups | cfu/ml | $\log_{10}$ reduction |
| --- | --- | --- |
| Gel Base (Control) | $4.7 \times 10^7$ | — |
| SA (2) | $1.9 \times 10^5$ | 2.4 |
| SEN (1) | $2.7 \times 10^5$ | 2.2 |
| PXE (1) | $1.8 \times 10^6$ | 1.4 |
| SEN (1) + SA (2) | $6.7 \times 10^1$ | 5.8 |
| PXE (1) + SA (2) | $9.3 \times 10^2$ | 4.7 |
| SEN (1) + PXE (1) | $1.0 \times 10^5$ | 2.7 |
| SEN (1) PXE (1) + SA (2) | $6.7 \times 10^1$ | 5.8 |

Notes:
Figures in brackets are the concentration of the ingredients (% w/w) that were added to Alcohol Gel Base-1.
SA: salicylic acid;
PXE: phenoxyethanol;
SEN: Sensiva ®.

The results presented in Tables 20 and 21 demonstrated that ESs and EOs or ICs show synergistic activity against both gram-negative and gram-positive microorganisms. These reagents, therefore, were chosen for incorporation into an alcohol-based gel for further study of the antimicrobial efficacy using the Pig Skin Model (PSM) developed in our laboratory. In these studies, the activities of these gels were evaluated and compared to alcohol-based gels having a similar composition but containing more traditional antimicrobials such as biguanides or quaternary ammonium compounds. Alcohol-based disinfectant gels containing synergistic combinations of ES and IC, or ES, IC, and AI were also tested.

For these studies, an alcohol gel-base (Alcohol Gel Base-2) having the following composition was prepared:

| Alcohol Gel Base - 2 | |
|---|---|
| Ingredient | % by weight |
| UCare JR 30M | 0.2 |
| Method 4-100 | 0.2 |
| Water | 35.15 |
| German Plus | 0.15 |
| Ethanol | 62.0 |
| Silicone (Dow Corning 245 fluid) | 0.5 |
| Incroquat Bethenyl TMS | 0.35 |
| Polawax A31 | 0.15 |
| Polawax A31 | 0.15 |
| Incroquat BA 85 | 0.3 |
| PPG-10 Cetylether (Procetyl-10) | 0.5 |
| Panthenol | 0.5 |

The ES, EO/IC and/or the AI then were incorporated into the Alcohol Gel Base-2 and the antimicrobial efficacy of the resultant formulation was evaluated in the Pig Skin Model (PSM) using the procedure described below.

The skin of freshly killed pig was obtained from a slaughterhouse, washed with water, dehaired, and defatted using scalpel. It was then cut into smaller sections, rinsed with water, and preserved in sealed plastic bags in a freezer. Before use, a section was removed, thawed, rinsed in water, and cut into pieces (3'3 cm) with a blade. These skin pieces were mounted on holders (plastic plates of 5 cm diameter) with epoxy to expose the skin surface. For each test, two pieces were used. One of the two pieces of pig skin was contaminated with $100\mu$ S. epidermidis ($10^8$ cfu/ml) and the two pieces were rubbed against each other for 15 sec. These pieces were then incubated at 37° C. for 3 hours. After the end of this period, the pieces were removed from the incubator and 0.1 ml of saline (0.9%) was applied on each skin piece and spread evenly on the skin with a glass rod. 50μ of the formulation gel was applied on each piece of the pig skin and the two skins were rubbed against each other for 15 sec. The two skin pieces were then left to dry for 1 minute. 0.1 ml of Triton X100 solution was applied to each of the pig skins and the two skins again were rubbed together for 15 sec. Each skin was rinsed with 4.9 ml of Triton X100 solution and the washings of each skin were separately collected in a Petri dish. The Triton-rinse collected from each of the pig skin pieces was then suitably diluted with Triton X100 solution and an aliquot was plated on D/E agar to determine microbial count. As a control, the skin was treated in a similar way except that PBS was used instead of test formulations. The results of these studies are shown in Tables 24 and 25.

TABLE 24

Antimicrobial activity of alcohol-based gel disinfectants containing ES and IC in a pig skin model
Test organism: S. epidermidis

| Formulation | Groups | Microbial count (cfu/ml) | $\log^{10}$ reduction |
|---|---|---|---|
| Control | Phosphate Buffered Saline (PBS) | $3.2 \times 10^6$ | — |
| Gel A | SEN (1.0) + F (0.5) + PXE (0.5) | $9.3\ 10^2$ | 3.5 |

TABLE 24-continued

Antimicrobial activity of alcohol-based gel disinfectants containing ES and IC in a pig skin model
Test organism: S. epidermidis

| Formulation | Groups | Microbial count (cfu/ml) | $\log^{10}$ reduction |
|---|---|---|---|
| Gel B | BZT (0.18) + F (0.5) | $1.5 \times 10^4$ | 2.3 |
| Gel C | PHMB (0.15) + F (0.5) | $1.3 \times 10^3$ | 3.4 |

Notes: Figures in brackets are the concentration of the ingredients (% w/w) that were added to Alcohol Gel Base-2.
SEN: Sensiva ®;
PXE: phenoxyethanol;
BZT; benzethonium chloride;
F: farnesol;
PHMB: a biguanide.

The Gel A formulation is able to produce 3.5-$\log_{10}$ reduction in microbial growth in the pig skin model (Table 24). Gel A does not contain any of the "traditional" antimicrobial agents such as biguanides or quaternary ammonium compounds; thus, the antimicrobial efficacy of Gel A is solely attributable to a synergistic combination of ES and ICs contained in this gel. The antimicrobial activity of Gel A is comparable to that of Gel C (a 3.4-$\log_{10}$ reduction in colony formation), which contains a biguanide (PHMB) along with the IC (farnesol), and is better than that of Gel B (a 2.3-$\log_{10}$ reduction in growth), which contains a quaternary ammonium compound (benzethonium chloride) along with the IC (farnesol). Hence, a combination of ES and IC can be used to confer antimicrobial properties to an alcohol-based gel formulation.

TABLE 25

Antimicrobial activity of alcohol-based gel disinfectants containing ES and IC in a pig skin model
Test organism: S. epidermidis

| Formulation | Groups | Microbial count (cfu/ml) | $\log^{10}$ reduction |
|---|---|---|---|
| Control | Phosphate Buffered Saline (PBS) | $4.2 \times 10^6$ | — |
| Gel D | SEN (1) + PXE (0.5) | $6.6 \times 10^4$ | 1.8 |
| Gel E | SEN (1) + PXE (0.5) + SA (1) | $8.8 \times 10^3$ | 2.7 |
| Gel F | SEN (1) + PXE (0.5) + F (0.3) | $1.1 \times 10^4$ | 2.6 |
| Gel G | SEN (1) + PXE (0.5) + F (0.3) + SA (1) | $4.6 \times 10^3$ | 3.0 |

Notes: Figures in brackets are the concentration of the ingredients (% w/w) that were added to Alcohol Gel Base-2.
SEN: Sensiva ®;
PXE: phenoxyethanol;
SA: salicylic acid;
F: farnesol.

Salicylic acid (an AI) enhances the activity of the ES/IC combination of Sensiva® and PXE from a 1.8- to a 2.7-$\log_{10}$ reduction in microbial growth (Table 25). Thus, a combination of ES, IC and AI also can be used to confer antimicrobial activity to an alcohol-based gel formulation.

Pig skin has been shown to have similar composition and behavior as that of human skin, and has been used in evaluating antimicrobial efficacy of skin disinfectants. See Bush L W, Benson L M, White J H. Pig skin as test substrate for evaluating topical antimicrobial activity. J Clin Microbiol 1986;24:343-48; Bissett D L, McBride J F. The use of the domestic pig as an animal model for human dry skin and for comparison of dry and normal skin properties. J. Soc Cosmet Chem 1983;34:317-26; Meyer W, Schwarz R, Neurand K. The skin of domestic pig. Curr. Problem Dematol 1978,7:39-

52. Thus it is anticipated that the same formulations can be used as hand-disinfectants for human-use.

Examples of disinfectant formulations containing ES and/or EO/IC and/or AI include the following:

Example 15-1

| | |
|---|---|
| UCare JR 30M | 0.2 |
| Methocel 40-100 | 0.2 |
| Water | 33.15 |
| Germall Plus | 0.15 |
| Ethanol | 62.0 |
| Silicone (Dow Corning 245 fluid) | 0.5 |
| Incroquat Behenyl TMS | 0.35 |
| Polawax A31 | 0.15 |
| Incroquat BA 85 | 0.3 |
| PPG-IO Cetyl ether (Procetyl-10) | 0.5 |
| Panthenol | 0.5 |
| Sensiva ® | 1.0 |
| Farnesol | 0.5 |
| Phenoxyethanol | 0.5 |

Example 15-2

| | |
|---|---|
| UCare JR 30M | 0.2 |
| Methocel 40-100 | 0.2 |
| Water | 33.35 |
| Germall Plus | 0.15 |
| Ethanol | 62.0 |
| Silicone (Dow Corning 245 fluid) | 0.5 |
| Incroquat Behenyl TMS | 0.35 |
| Polawax A31 | 0.15 |
| Incroquat BA 85 | 0.3 |
| PPG-IO Cetyl ether (Procetyl-10) | 0.5 |
| Panthenol | 0.5 |
| Sensiva ® | 1.0 |
| Farnesol | 0.5 |
| Phenoxyethanol | 0.5 |

Example 15-3

| | |
|---|---|
| UCare JR 30M | 0.2 |
| Methocel 40-100 | 0.2 |
| Water | 32.35 |
| Germall Plus | 0.15 |
| Ethanol | 62.0 |
| Silicone (Dow Corning 245 fluid) | 0.5 |
| Incroquat Behenyl TMS | 0.35 |
| Polawax A31 | 0.15 |
| Incroquat BA 85 | 0.3 |
| PPG-IO Cetyl ether (Procetyl-10) | 0.5 |
| Panthenol | 0.5 |
| Sensiva ® | 1.0 |
| Farnesol | 0.3 |
| Phenoxyethanol | 0.5 |
| Salicylic acid | 1.0 |

Various publications and have been referenced herein, the contents of which are hereby incorporated by reference in their entireties.

What is claimed:

1. A topical composition comprising two or more water-soluble, organic salts of zinc at concentrations between 0.1% and 2% (w/w), wherein the water-soluble, organic salts of zinc are selected from the group consisting of zinc acetate, zinc butyrate, zinc citrate, zinc gluconate, zinc glycerate, zinc glycolate, zinc formate, zinc lactate, zinc picolinate, zinc proprionate, zinc tartrate and zinc undecylenate, between 0.2% and 5% panthenol, between 0.2% and 3% (w/w) octoxyglycerin, and between 1.0% and 4% salicylic acid, wherein the amounts of octoxyglycerin and salicylic acid exhibit a synergistic antimicrobial activity.

2. The topical composition of claim 1, wherein the zinc salts are present in an amount effective in reducing or preventing irritation.

3. The topical composition of claim 1, further comprising an essential oil or active component thereof.

4. A topical composition comprising two or more water-soluble, organic salts of zinc at concentrations between 0.1% and 2% (w/w), wherein the water-soluble, organic salts of zinc are selected from the group consisting of zinc acetate, zinc butyrate, zinc citrate, zinc gluconate, zinc glycerate, zinc glycolate, zinc formate, zinc lactate, zinc picolinate, zinc proprionate, zinc tartrate and zinc undecylenate, salicylic acid and between 0.2% and 5% panthenol.

* * * * *